(12) United States Patent
Jin

(10) Patent No.: US 8,354,539 B2
(45) Date of Patent: Jan. 15, 2013

(54) INDOLE DERIVATIVES AS IKK2 INHIBITORS

(75) Inventor: Qi Jin, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/255,264

(22) PCT Filed: Mar. 8, 2010

(86) PCT No.: PCT/EP2010/052885
§ 371 (c)(1),
(2), (4) Date: Sep. 8, 2011

(87) PCT Pub. No.: WO2010/102968
PCT Pub. Date: Sep. 16, 2010

(65) Prior Publication Data
US 2012/0010244 A1    Jan. 12, 2012

Related U.S. Application Data

(60) Provisional application No. 61/158,860, filed on Mar. 10, 2009.

(51) Int. Cl.
*C07D 401/00*   (2006.01)
*A61K 31/54*   (2006.01)

(52) U.S. Cl. ...................... 546/201; 514/323

(58) Field of Classification Search ............... 546/201; 514/323
See application file for complete search history.

(56) References Cited

U.S. PATENT DOCUMENTS

| | | | |
|---|---|---|---|
| 4,775,761 A | 10/1988 | Strupczewski | |
| 5,026,856 A | 6/1991 | Yatsunami et al. | |
| 5,254,473 A | 10/1993 | Patel | |
| 5,256,673 A | 10/1993 | Böttcher et al. | |
| 5,330,986 A | 7/1994 | Shutske | |
| 6,245,799 B1 | 6/2001 | Asselin et al. | |
| 6,358,994 B1 | 3/2002 | Fritz et al. | |
| 6,509,340 B1 | 1/2003 | Van Amsterdam et al. | |
| 6,589,954 B1 | 7/2003 | Mavunkel et al. | |
| 6,787,535 B2 | 9/2004 | Beard et al. | |
| 6,919,335 B2 | 7/2005 | Iwanowicz et al. | |
| 7,176,231 B2 | 2/2007 | Heckel et al. | |
| 7,375,219 B2 | 5/2008 | Maddaford et al. | |
| 2002/0103229 A1 | 8/2002 | Bhagwat et al. | |
| 2002/0147189 A1 | 10/2002 | Cai et al. | |
| 2002/0161004 A1 | 10/2002 | Browner et al. | |
| 2003/0022898 A1 | 1/2003 | Burke et al. | |
| 2005/0009876 A1 | 1/2005 | Bhagwat | |
| 2005/0153966 A1 | 7/2005 | Gangloff et al. | |
| 2005/0165086 A1 | 7/2005 | Callahan et al. | |
| 2006/0116419 A1 | 6/2006 | Callahan et al. | |
| 2006/0281836 A1 | 12/2006 | Kerns | |
| 2007/0254873 A1 | 11/2007 | Kerns et al. | |
| 2007/0281933 A1 | 12/2007 | Kerns et al. | |
| 2008/0146606 A1 | 6/2008 | Bamborough et al. | |
| 2008/0242685 A1 | 10/2008 | Kerns et al. | |
| 2008/0262040 A1 | 10/2008 | Callahan et al. | |
| 2008/0269291 A1 | 10/2008 | Kerns et al. | |
| 2008/0293802 A1 | 11/2008 | Kerns et al. | |
| 2009/0030014 A1 | 1/2009 | Kugimiya et al. | |
| 2009/0143372 A1 | 6/2009 | Kerns et al. | |
| 2010/0130468 A1 | 5/2010 | Busch-Petersen et al. | |
| 2010/0179139 A1 | 7/2010 | Bamborough et al. | |

FOREIGN PATENT DOCUMENTS

| | | |
|---|---|---|
| DE | 3342632 | 6/1985 |
| DE | 19500689 | 7/1996 |
| DE | 19807993 | 9/1999 |
| DE | 19928424 | 12/2000 |
| DE | 10112151 | 9/2002 |
| DE | 10259244 | 7/2004 |
| EP | 279263 | 8/1993 |
| EP | 0556949 A2 | 8/1993 |
| EP | 610134 | 8/1994 |
| EP | 416609 | 1/1997 |
| EP | 0812826 | 12/1997 |
| EP | 1077213 | 2/2001 |
| EP | 1134221 | 9/2001 |
| EP | 1209158 | 5/2002 |
| JP | A-60-132980 | 7/1985 |
| JP | A-2002-533333 | 10/2002 |
| WO | WO94/21627 | 9/1994 |
| WO | WO94/21630 | 9/1994 |
| WO | WO96/40115 | 12/1996 |
| WO | WO97/44319 | 11/1997 |
| WO | WO98/06715 | 2/1998 |
| WO | WO98/28292 | 7/1998 |
| WO | WO99/43652 | 2/1999 |
| WO | WO99/17773 | 4/1999 |
| WO | WO00/00487 | 1/2000 |
| WO | WO01/00610 | 1/2001 |
| WO | WO01/30774 | 5/2001 |
| WO | WO01/34598 | 5/2001 |
| WO | WO01/58890 | 8/2001 |
| WO | WO01/68648 | 9/2001 |
| WO | WO01/83472 | 11/2001 |
| WO | WO01/87298 | 11/2001 |
| WO | WO01/98290 | 12/2001 |

(Continued)

OTHER PUBLICATIONS

U.S. Appl. No. 10/597,154, filed Jul. 13, 2006, Baldwin et al.
U.S. Appl. No. 11/931,189, filed Oct. 31, 2007, Deng et al.
U.S. Appl. No. 11/570,060, filed Dec. 5, 2006, Jeffrey K. Kerns.
U.S. Appl. No. 11/575,416, filed Mar. 16, 2007, Kerns et al.
U.S. Appl. No. 12/093,750, filed May 15, 2008, Kerns et al.
U.S. Appl. No. 12/096,397, filed Jun. 6, 2008, Kerns et al.
U.S. Appl. No. 12/532,773, filed Sep. 23, 2009, Busch-Petersen et al.
Aupperle et al., "NF-κB Regulation by IκB Kinase in Primary Fibroblast-Like Synoviocytes" *J. Immunology* (1999) 163:427-433.
Aupperle et al., "NF-κB Regulation by IκB Kinase-2 in Rheumatoid Arthritis Synoviocytes" *J. Immunology* (2001) 166:31496-31501.
Aupperle, J. Immunology 2001; 166: 2705-11.
Baxter, Bioorg. Med. Chem. Lett., 14, 2817-2822 (2004).

(Continued)

*Primary Examiner* — Janet Andres
*Assistant Examiner* — John Mabry
(74) *Attorney, Agent, or Firm* — Nora L. Stein; Theodore R. Furman

(57) ABSTRACT

The invention is directed to a certain novel compound which is an inhibitor of kinase activity, in particular IKK2 activity.

10 Claims, 3 Drawing Sheets

FOREIGN PATENT DOCUMENTS

| | | |
|---|---|---|
| WO | WO02/14317 | 2/2002 |
| WO | WO02/16353 | 2/2002 |
| WO | WO02/24679 | 3/2002 |
| WO | WO02/24693 | 3/2002 |
| WO | WO02/28860 | 3/2002 |
| WO | WO02/30353 | 4/2002 |
| WO | WO02/30423 | 4/2002 |
| WO | WO02/41843 | 5/2002 |
| WO | WO02/44153 | 6/2002 |
| WO | WO02/46171 | 6/2002 |
| WO | WO02/051837 | 7/2002 |
| WO | WO02/060386 | 8/2002 |
| WO | WO02/094265 | 11/2002 |
| WO | WO02/094322 | 11/2002 |
| WO | WO02/094813 | 11/2002 |
| WO | WO03/07076 | 1/2003 |
| WO | WO03/010158 | 2/2003 |
| WO | WO03/010163 | 2/2003 |
| WO | WO03/022898 | 3/2003 |
| WO | WO03/024935 | 3/2003 |
| WO | WO03/024936 | 3/2003 |
| WO | WO03/027075 | 4/2003 |
| WO | WO03/035625 | 5/2003 |
| WO | WO03/037664 | 5/2003 |
| WO | WO03/037886 | 5/2003 |
| WO | WO03/068193 A | 8/2003 |
| WO | WO03/084959 | 10/2003 |
| WO | WO03/087087 | 10/2003 |
| WO | WO03/095430 | 11/2003 |
| WO | WO03/101987 | 12/2003 |
| WO | WO03/103661 | 12/2003 |
| WO | WO03/104218 | 12/2003 |
| WO | WO2004/019935 | 3/2004 |
| WO | WO2004/022553 | 3/2004 |
| WO | WO2004/024730 | 3/2004 |
| WO | WO2004/024732 | 3/2004 |
| WO | WO2004/024736 | 3/2004 |
| WO | WO2004/047760 | 6/2004 |
| WO | WO2004/075846 | 9/2004 |
| WO | WO2004/089913 | 10/2004 |
| WO | WO2004/106293 | 12/2004 |
| WO | WO2005/012283 | 2/2005 |
| WO | WO2005/035527 | 4/2005 |
| WO | WO2005/035537 | 4/2005 |
| WO | WO2005/067923 | 7/2005 |
| WO | WO2006/002434 | 1/2006 |
| WO | WO 2006/034317 | 3/2006 |
| WO | WO2006/106326 | 10/2006 |
| WO | WO2007/005534 | 1/2007 |
| WO | WO 2007/005534 A2 | 1/2007 |
| WO | WO2007/010964 | 1/2007 |
| WO | WO 2007/114848 A2 | 10/2007 |
| WO | WO2009/112473 | 9/2009 |
| WO | WO2010/102968 | 9/2010 |
| WO | WO2010/106016 | 9/2010 |

OTHER PUBLICATIONS

Breton et al., "The Natural Product Hymenialdisine Inhibits Interleukin-8 Production in U937 Cells by Inhibition of Nuclear Factor-κB" *JPET* (1997) 282(1):459-466.

Burke et al., "BMS-345541 Is a Highly Selective Inhibitor of $I_KB$ Kinase That Binds at an Allosteric Site of the Enzyme and Blocks NF-κB-dependent Transcription in Mice" *J. Biol Chem.* (2003) 278:1450-1456.

Guttridge et al., "NF-κB-Induced Loss of *MyoD* Messenger RNA: Possible Role in Muscle Decay and Cachexia" *Science* (2000) 289:2363-2365.

Micallef., et al., "Brominated isoindolines: Precursors to functionalised nitroxides", *Journal of the Chemical Society* Perkin 2, (001), 65 and 72, 1999.

Miller, et al., "3,5-Disubstituted-indole-7-carboxamides: The Discovery of a novel series of potent, selective inhibitors of IKK-β", *Bioorganic & Medicine Chemistry Letters* 21 (2011) 2255-2258.

Murata et al., "Discovery of novel and selective IKK-β serine-threonine protein kinase inhibitors. Part 1." *Bioorg. Med. Chem. Letter* (2003) 13:913-198.

Murata et al., "*Synthesis and structure—activity relationships of novel IKK-62 inhibitors. Part 2: Imrovement of in vitro activity*" Bioorg. Med. Chem. Letter (2004) 14(15):4013-4017.

Murata et al., "*Synthesis and structure—activity relationships of novel IKK-β inhibitors. Part 3: Orally active anti-inflammatory agents*," Bioorg. Med. Chem. Letter (2004) 14(15):4019-4022.

Peet et al., "IκB Kinases α and β Show a Random Sequential Kinetic Mechanism and Are Inhibited by Staurosporine and Quercetin" J. Biol. Chem. (1999) 274:32655-32661.

Pharmaceutical Research, 1986, vol. 3, No. 6, 318.

Pierce, et al., "Novel Inhibitors of Cytokine-induced IκBα Phosphorylation and Endothelial Cell Adhesion Molecule Expression Show Anti-inflammatory Effects in Vivo" J. Biol. Chem. (1997) 272:21096-21103.

Protecting Groups in organic Synthesis; TW Green, PG M Wuts, John Wiley & Sons, 1991.

Roshak, et al., "Inhibition of NFκB-Mediated Interleukin-1β-Stimulated Prostaglandin E2 Formation by the Marine Natural Product Hymenialdisine" JPET (1997) 283(2):955-961.

Roshak, et al., "Manipulation of Distinct NFκB Proteins Alters Interleukin-1β-induced Human Rheumatoid Synovial Fibroblast Prostaglandin E2 Formation" J. Biol. Chem. (1996) 271:31496-31501.

Stereochemistry of Organic Compounds, TW Green, P G M Wuts, E L ELeil, S H Wile, L N Mander, Wiley-Interscience, 1994.

Sullivan et al., "2-Chloro-4-(trifluoromethyl)pyrimidine-5-N-(3',5'-bis(trifluoromethyl)phenyl)- carboxamide: A Potent Inhibitor of NF-κB- and AP-1-Mediated Gene Expression Identified Using Solution-Phase Combinatorial Chemistry" J. Med. Chem. (1998) 41:413-419.

Tak et al., "Inhibitor of nuclear factor κB kinase β is a key regulator of synovial inflammation" Arthritis and Rheumatism (2001) 44(8):1897-1907.

Baldwin, CA 143:172 754 (Jul. 2005).

Wahl et al., "Sulfasalazine: a potent and specific inhibitor of nuclear factor kappa B" J. Clin. Invest.(1998) 101(5):1163-1174.

Wisniewski et al., "*Assay for IκB Kinases Using an in Vivo Biotinyiated IκB Protein Substrate*" Analytical Biochem. (1999) 274:220-228.

Boettcher, et al., Abstract No. 98323-88-7 (Sep. 29, 1985).

C. G. Wermuth. *The Practice of Medicinal Chemistry*, Academic Press, pp. 203-214 (1996).

Restriction Requirement dated May 20, 2009 in U.S. Appl. No. 10/597,154.

Official Action dated Oct. 27, 2009 in U.S. Appl. No. 10/597,154.

Final Action dated Jul. 15, 2010 in U.S. Appl. No. 10/597,154.

Official Action dated Mar. 31, 2011 in U.S. Appl. No. 10/597,154.

Official Action dated May 20, 2010 in U.S. Appl. No. 11/570,060.

Restriction Requirement dated Dec. 15, 2009 in U.S. Appl. No. 11/570,060.

Final Action dated Oct. 21, 2010 in U.S. Appl. No. 11/570,060.

Advisory Action dated Feb. 10, 2011 in U.S. Appl. No. 11/570,060.

Notice of Allowance dated May 2, 2011 in U.S. Appl. No. 11/570,060.

RCE dated Jul. 22, 2011 in U.S. App. No. 11/570,060.

Final Action dated May 14, 2009 in U.S. Appl. No. 11/575,416.

Official Action dated Jan. 4, 2010 in U.S. Appl. No. 11/575,416.

Notice of Allowance dated Aug. 11, 2010 in U.S. Appl. No. 11/575,416.

Restriction dated Apr. 6, 2010 in U.S. Appl. No. 11/931,189.

Official Action dated Aug. 23, 2010 in U.S. Appl. No. 11/931,189.

Notice of Allowance dated Jan. 31, 2011 in U.S. Appl. No. 11/931,189.

RCE dated May 2, 2011 in U.S. Appl. No. 11/931,189.

Notice of Allowance dated Jul. 14, 2011 in U.S. Appl. No. 11/931,189.

Restriction Requirement dated Aug. 26, 2010 in U.S. Appl. No. 12/093,750.

Official Action dated Dec. 16, 2010 in U.S. Appl. No. 12/093,750.

Official Action dated Jun. 2, 2011 in U.S. Appl. No. 12/093,750.

Official Action dated May 26, 2011 in U.S. Appl. No. 12/096,397.

Notice of Allowance dated Mar. 14, 2011 in U.S. Appl. No. 12/532,773.

RCE dated Jun. 14, 2011 in U.S. Appl. No. 12/532,773.

Notice of Allowance dated Jul. 22, 2011 in U.S. Appl. No. 12/532,773.

INDOLE DERIVATIVES AS IKK2 INHIBITORS

This application is a 371 national phase entry of International Application No. PCT/EP2010/052885, filed Mar. 8, 2010, which claims the benefit of U.S. Provisional Application No. 61/158,860, filed Mar. 10, 2009, which is incorporated herein in its entirety.

FIELD OF THE INVENTION

The invention is directed to a novel compound which is an inhibitor of kinase activity. More specifically, the compound is an IKK2 inhibitor. Compounds which are IKK2 inhibitors may be useful in the treatment of disorders associated with inappropriate IKK2 (also known as IKKβ) activity, in particular in the treatment and prevention of disorders mediated by IKK2 mechanisms including inflammatory and tissue repair disorders, fibrotic diseases and dermatosis. Such disorders include COPD (chronic obstructive pulmonary disease) and asthma.

BACKGROUND OF THE INVENTION

An important large family of enzymes is the protein kinase enzyme family. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK) include cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also in progress to identify modulators of tyrosine kinases as well.

Nuclear factor κB (NF-κB) represents a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p52/p100), c-Rel, and RelB, all of which can form hetero- or homo-dimers. These proteins share a highly homologous 300 amino acid "Rel homology domain" which contains the DNA binding and dimerization domains. The NFkBs also carry a nuclear localisation sequence near the C-terminus of the Rel homology domain which is important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκBα and β for example, are phosphorylated on two N-terminal serines by the recently identified IκB kinases (IKK-α and IKK-β), whilst NF-κB2, which carries an IkB-like C terminal region is phosphorylated on N and C terminal serines by IKK-α. IKK-β is also known as IKK2 and its now widely accepted that it is essential for rapid NFkB activation in response to pro-inflammatory stimuli. IKK2 is an example of a serine/threonine kinase. Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoregualtory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele, K. R., et al., *J. Immunology*, 1999, 163:427-433 and Aupperle, K. R, et al., *J. Immunology*, 2001, 166: 2705-11. More recently, the intra-articular administration of a wild type IKK-β adenoviral construct was shown to cause paw swelling while intra-articular administration of dominant-negative IKKβ inhibited adjuvant-induced arthritis in rat. See Tak, P. P., et al., *Arthritis and Rheumatism*, 2001, 44:1897-1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytokine-induced muscle wasting (Guttridge, D. C., et al., *Science*, 2000, 289: 2363-2365) further supporting the potential of NFκB inhibitors as novel cancer therapies.

Several NF-κB and IKK inhibitors are described in Wahl, C., et al., *J. Clin. Invest.* 101(5), 1163-1174 (1998); Sullivan, R. W., et al., *J. Med. Chem.*, 41, 413-419 (1998); Pierce, J. W., et al., *J. Biol. Chem.* 272, 21096-21103 (1997); and Coish, P. D. G., et al., *Expert Opin. Ther. Patents*, 2006, vol 16(1) 1-12.

The marine natural product hymenialdisine is known to inhibit NF-κB. See Roshak, A., et al., *JPET*, 283, 955-961 (1997); and Breton, J. J., and Chabot-Fletcher, M. C., *JPET*, 282, 459-466 (1997).

Attempts have been made to prepare compounds that inhibit IKK2 activity and a number of such compounds have been disclosed in the art. However, in view of the number of pathological responses that are mediated by IKK2, there remains a continuing need for inhibitors of IKK2 which can be used in the treatment of a variety of conditions.

The present inventors have discovered a novel compound which is an inhibitor of kinase activity, in particular IKK2 activity. Compounds which are IKK2 inhibitors may be useful in the treatment of disorders associated with inappropriate kinase activity, in particular inappropriate IKK2 activity, for example in the treatment and prevention of disorders mediated by IKK2 mechanisms. Such disorders include inflammatory and tissue repair disorders (including rheumatoid arthritis, inflammatory bowel disease, COPD (chronic obstructive pulmonary disease), asthma and rhinitis), fibrotic diseases, osteoarthritis, osteoporosis, dermatosis (including psoriasis, atopic dermatitis and ultraviolet radiation (UV)-induced skin damage), autoimmune diseases (including Sjogren's syndrome, systemic lupus eythematosus, multiple sclerosis, psoriatic arthritis, alkylosing spondylitis, tissue and organ rejection), Alzheimer's disease, stroke, atherosclerosis, restonosis, diabetes, glomerulonephritis, cancer (including Hodgkins disease), cachexia, inflammation associated with infection and certain viral infections (including acquired immune deficiency syndrome (AIDS)), adult respiratory distress syndrome, and Ataxia Telangiestasia. In particular, the disorders include inflammatory and tissue repair disorders (including inflammatory bowel disease, COPD (chronic obstructive pulmonary disease), asthma and rhinitis), fibrotic diseases and dermatosis (including psoriasis, atopic dermatitis and ultraviolet radiation (UV)-induced skin damage).

Further, the compound of formula (I), or a salt thereof, may show an improved profile over known IKK2 inhibitors in that it may possess one or more of the following properties:
(i) potent IKK2 activity with a pIC$_{50}$ of greater than about 7.0;
(ii) selective for the IKK2 receptor over the IKK1 receptor; and/or
(iii) low CNS penetration.

Compounds having such a profile may be effective when inhaled, and/or capable of once daily administration and/or further may have an improved side effect profile compared with other existing therapies.

The compound of formula (I), or a salt thereof, may have an improved safety profile over known IKK2 inhibitors. In particular, the compound of formula (I), or a salt thereof, may possess an improved toxicity profile when compared to known IKK2 inhibitors.

In one embodiment, the compound may show selectivity for IKK2 over other kinases.

In one embodiment, the compound may be suitable for development as a drug due to its pharmacokinetic profile.

SUMMARY OF THE INVENTION

The invention is directed to a novel compound. Specifically, the invention is directed to 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide of formula (I):

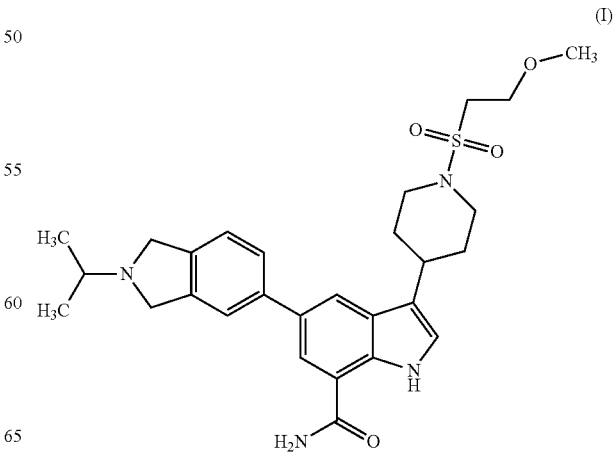

or a salt thereof.

The compound of formula (I), or a salt thereof, is an inhibitor of IKK2 activity. Compounds which are IKK2 inhibitors may be useful in the treatment of disorders associated with inappropriate IKK2 (also known as IKKβ) activity, such as COPD (chronic obstructive pulmonary disease) and asthma. Accordingly, the invention is further directed to pharmaceutical compositions comprising the compound of formula (I) or a pharmaceutically acceptable salt thereof. The invention is still further directed to methods of inhibiting IKK2 activity and treatment of disorders associated therewith using the compound of formula (I), or a pharmaceutically acceptable salt thereof, or a pharmaceutical composition comprising the compound of formula (I) or a pharmaceutically acceptable salt thereof.

DETAILED DESCRIPTION OF THE INVENTION

Figure 1:
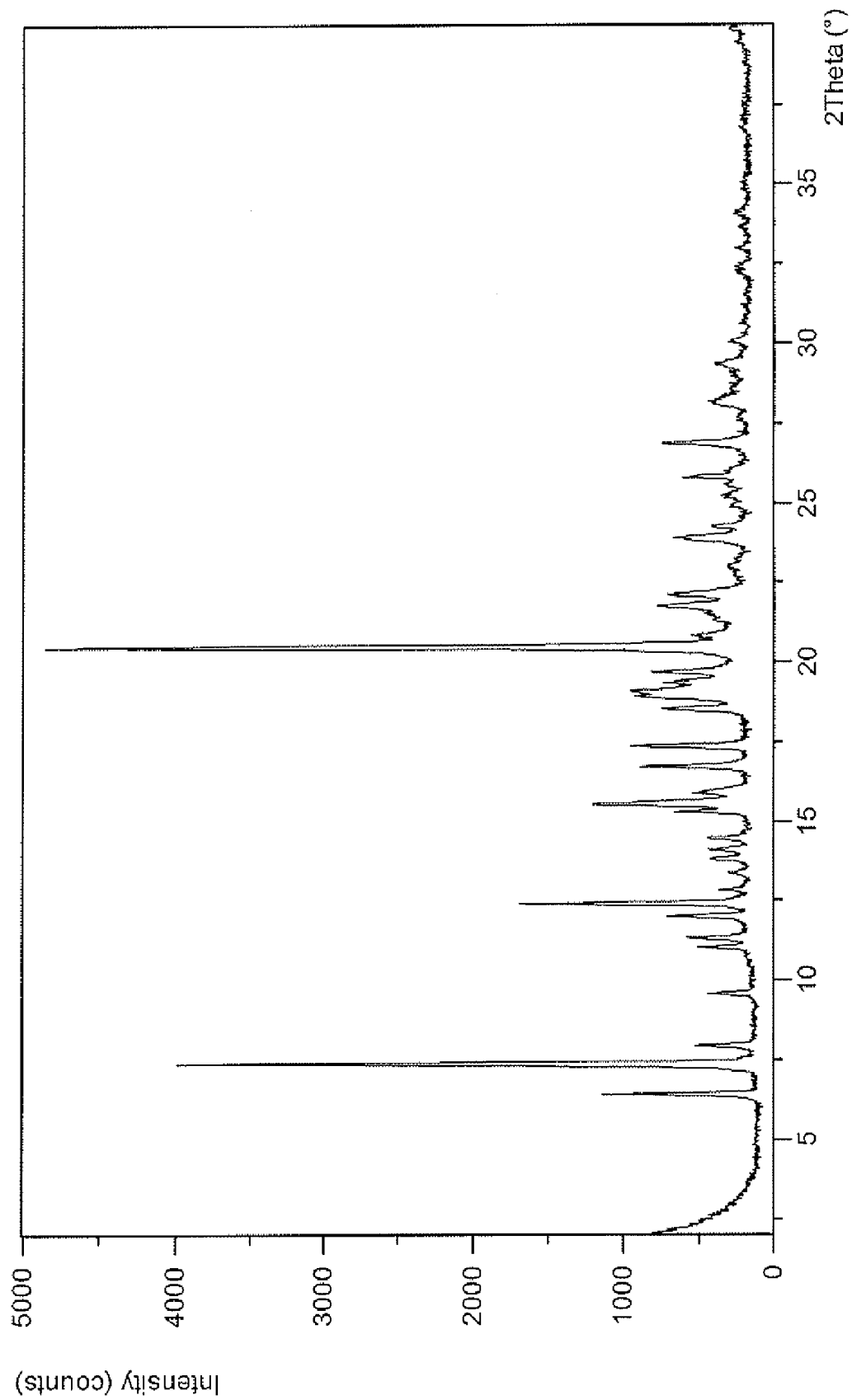
FIG. 1 shows the XRPD (X-Ray Powder Diffraction) pattern of Example 1.

In one aspect, the invention is directed 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide of formula (I):

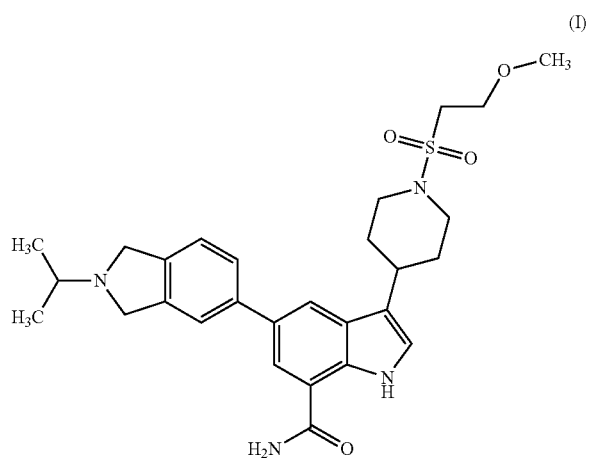 [SMILES: COCCS(=O)(=O)N1CCC(c2c[nH]c3c(C(N)=O)cc(-c4ccc5c(c4)CN(C(C)C)C5)cc23)CC1]

or a salt thereof.

Included within the scope of the invention are all solvates (including hydrates), complexes, polymorphs, prodrugs, and radiolabelled derivatives of the compound of formula (I), or a salt thereof.

The compound of formula (I), or a salt thereof, is typically in solid form. In the solid state, the compound of formula (I), or a salt thereof, may exist in crystalline or noncrystalline form, or as a mixture thereof. For the compound of formula (I), or a salt thereof, in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that the compound of formula (I), or a salt thereof, in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

In one aspect, the present invention provides 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide, or a salt thereof, in crystalline form.

In one embodiment, the present invention provides 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide in crystalline form.

In another embodiment, the present invention provides crystalline 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide characterised in that it provides:
  (i) an XRPD (X-ray powder diffraction) pattern having peaks (°2θ) at about 6.4, about 7.4, about 12.4, about 15.6 and about 20.5; and/or
  (ii) a DSC (differential scanning calorimetry) thermogram having a melt with combined degredation with an onset temperature of about 115° C.

In another embodiment, the present invention provides crystalline 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide characterised in that it provides:
  (i) an XRPD (X-ray powder diffraction) pattern having peaks (°2θ) at 6.4±0.1°2θ, 7.4±0.1°2θ, 12.4±0.1°2θ, 15.6±0.1°2θ and 20.5±0.1°2θ; and/or
  (ii) a DSC (differential scanning calorimetry) thermogram having a melt with combined degredation with an onset temperature of 115° C.

In another embodiment, the present invention provides crystalline 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide characterised in that it provides an XRPD pattern substantially in accordance with FIG. 1.

In a further embodiment, the present invention provides crystalline 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide characterised in that it provides an XRPD pattern comprising peaks substantially as set out in Table 1.

Figure 2:
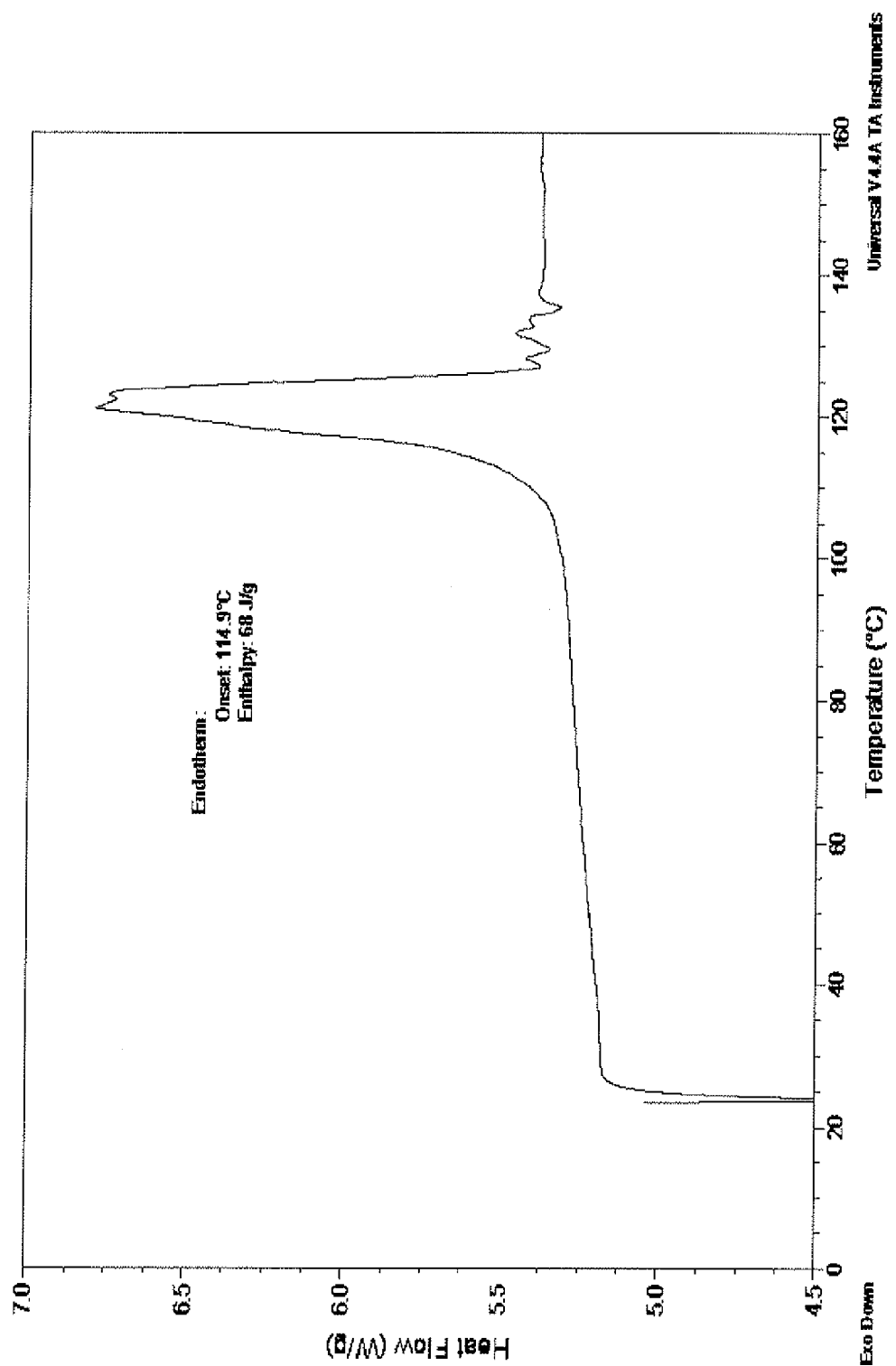
FIG. 2 shows the DSC (Differential Scanning Calorimetry) of Example 1.

In another embodiment, the present invention provides crystalline 5-[2-(1-methylethyl)-2,3-dihydro-1H-isoindol-5-yl]-3-(1-{[2-(methyloxy)ethyl]sulfonyl}-4-piperidinyl)-1H- indole-7-carboxamide characterised in that it provides a DSC thermogram substantially in accordance with FIG. 2.

The invention also includes isotopically-labelled compounds, which are identical to the compound of formula (I), or a salt thereof, but for the fact that one or more atoms are replaced by an atom having an atomic mass or mass number different from the atomic mass or mass number most commonly found in nature. Examples of isotopes that can be incorporated into the compound of formula (I), or a salt thereof, include isotopes of hydrogen, carbon, nitrogen and oxygen, such as 3H, 11C and 14C.

It is to be understood that the references herein to compound of formula (I) or a salt thereof covers the compound of formula (I) as the free base or as salts thereof, for example as a pharmaceutically acceptable salt thereof.

The skilled artisan will appreciate that pharmaceutically acceptable salts of the compound according to formula (I) may be prepared. Indeed, in certain embodiments of the invention, pharmaceutically acceptable salts of the compound according to formula (I) may be preferred over the respective free base or free acid because such salts impart greater stability or solubility to the molecule thereby facilitating formulation into a dosage form. Accordingly, the invention is further directed to the compound of formula (I) or a pharmaceutically acceptable salt thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free base form with a suitable acid.

Salts and solvates having non-pharmaceutically acceptable counter-ions or associated solvents are within the scope of the present invention, for example, for use as intermediates in the preparation of the compound of formula (I) and its pharmaceutically acceptable salts. Thus one embodiment of the invention embraces the compound of formula (I) and salts thereof.

In certain embodiments, the compound according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In one embodiment, the pharmaceutically acceptable acid addition salt is a hydrochloride.

Compound Preparation

The compound of formula (I), or a salt thereof, may be made by a variety of methods, including standard chemistry.

The compound of formula (I) may be prepared according to Scheme 1, by reacting 5-bromo-3-(1-{[2-(methyloxy) ethyl]sulfonyl}-4-piperidinyl)-1H-indole-7-carboxamide with [2-(1-methylethyl)-2,3-dihydro-1H-isoindol-5-yl]boronic acid. Suitable conditions comprise treatment with a suitable base, such as potassium carbonate, in a suitable solvent or solvent mixture, such as 1,4-dioxane and water, followed by the addition a palladium catalyst, such as PdCl$_2$(dppf)-CH$_2$Cl$_2$), and subsequently heating the mixture at a suitable temperature until the reaction has gone to completion (for example at about 90° C. for about 1.5 hours).

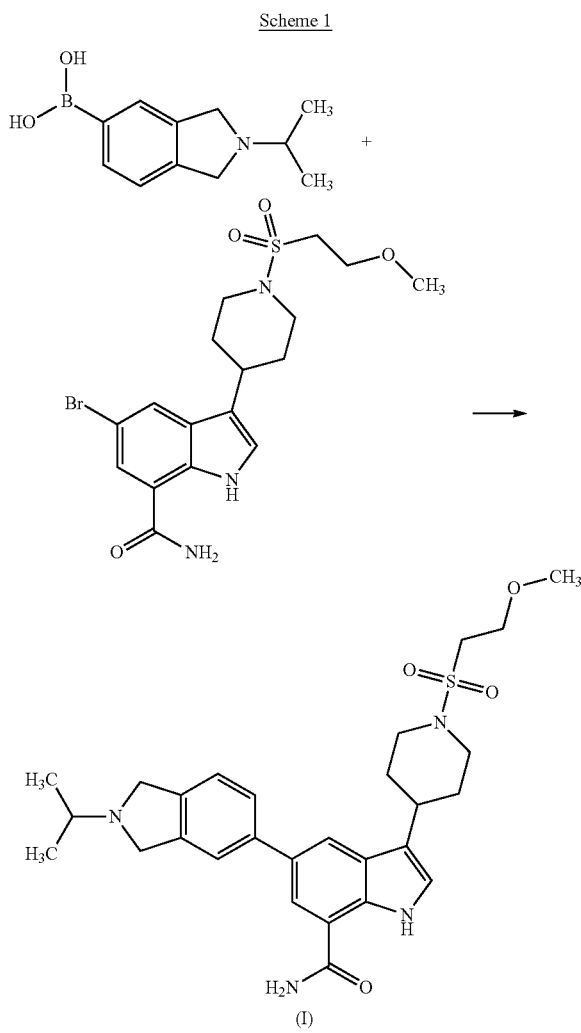

Scheme 1

Alternatively, the compound of formula (I) may be prepared according to Scheme 2, by reacting 5-bromo-2-(1-methylethyl)-2,3-dihydro-1H-isoindole, or a salt thereof, such as the hydrochloride salt, with 3-(1-{[2-(methyloxy)ethyl] sulfonyl}-4-piperidinyl)-5-(4,4,5,5-tetramethyl-1,3,2-dioxaborolan-2-yl)-1H-indole-7-carboxamide, or a solvate thereof, such as the dioxane solvate. Suitable conditions comprise treatment with a suitable base, such as potassium phosphate tribasic monohydrate, in a suitable solvent or solvent mixture, such as 1,4-dioxane and water, followed by the addition of a palladium catalyst, such as tris(dibenzylideneacetone)dipalladium(0), and a suitable ligand, such as 2-Dicyclohexylphosphino-2',4',6'-triisopropylbiphenyl (XPhos). The reaction mixture is heating to a temperature just under reflux and maintained at this temperature until the reaction has gone to completion.

Scheme 2

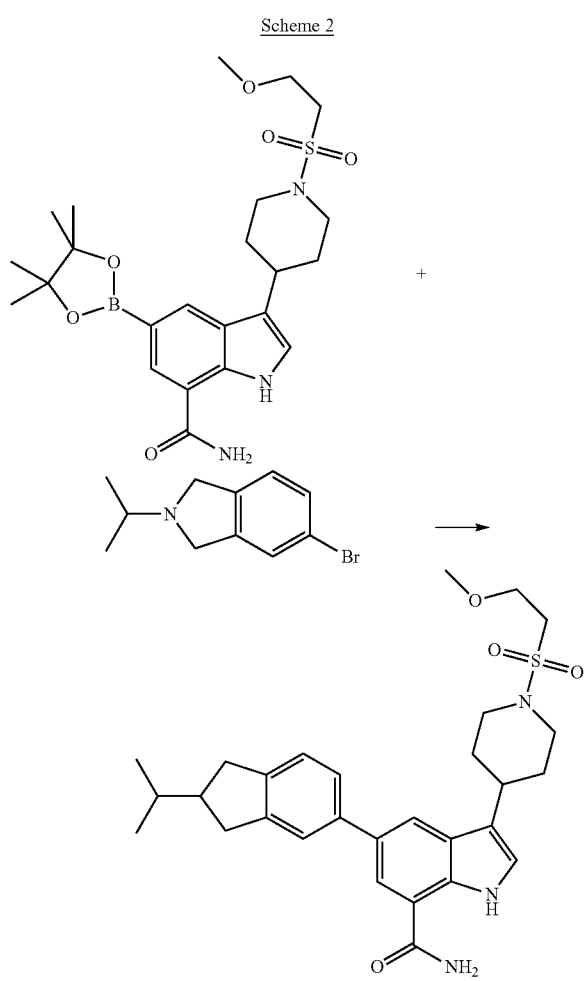

Methods of Use

The compound of formula (I), or a salt thereof, is an inhibitor of IKK2. Compounds which are IKK2 inhibitors may be useful in the treatment of disorders wherein the underlying pathology is (at least in part) attributable to inappropriate IKK2 (also known as IKKβ) activity such as COPD (chronic obstructive pulmonary disease) and asthma. "Inappropriate IKK2 activity" refers to any IKK2 activity that deviates from the normal IKK2 activity expected in a particular patient. Inappropriate IKK2 activity may take the form of, for instance, an abnormal increase in activity, or an aberration in the timing and or control of IKK2 activity. Such inappropriate activity may result then, for example, from overexpression or mutation of the protein kinase leading to inappropriate or uncontrolled activation. Accordingly, in another aspect the invention is directed to methods of treating such disorders.

Such disorders include inflammatory and tissue repair disorders (including inflammatory bowel disease, COPD (chronic obstructive pulmonary disease), asthma and rhinitis), fibrotic diseases and dermatosis (including psoriasis, atopic dermatitis and ultraviolet radiation (UV)-induced skin damage).

The methods of treatment of the invention comprise administering a safe and effective amount of the compound of formula (I), or a pharmaceutically acceptable salt thereof, to a human in need thereof. Individual embodiments of the invention include methods of treating any one of the above-mentioned disorders by administering a safe and effective amount of the compound of formula (I), or a pharmaceutically acceptable salt thereof, to a human in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to the compound of formula (I), or a pharmaceutically acceptable salt thereof, or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

The compound of formula (I), or a pharmaceutically acceptable salt thereof, may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compound of formula (I), or a pharmaceutically acceptable salt thereof, may be administered orally. In another embodiment, the compound of formula (I), or a pharmaceutically acceptable salt thereof, may be administered by inhalation. In a further embodiment, the compound of formula (I), or a pharmaceutically acceptable salt thereof, may be administered intranasally.

The compound of formula (I), or a pharmaceutically acceptable salt thereof, may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of formula (I), or a pharmaceutically acceptable salt thereof, depend on the pharmacokinetic properties of the compound, such as absorption, distribution, and half-life, which can be determined by the skilled artisan. In addition, suitable dosing regimens, including the duration such regimens are administered, for the compound of formula (I), or a pharmaceutically acceptable salt thereof, depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compound of formula (I) may be administered as a prodrug. As used herein, a "prodrug" of the compound of formula (I) is a functional derivative of the compound which, upon administration to a patient, eventually liberates the compound of formula (I) in vivo. Administration of the compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate IKK2 activity comprising administering a safe and effective amount of the compound of formula (I) or a pharmaceutically acceptable salt thereof to a human in need thereof.

In one embodiment, the disorder mediated by inappropriate IKK2 activity is selected from the group consisting of inflammatory and tissue repair disorders (including inflammatory bowel disease, COPD (chronic obstructive pulmonary disease), asthma and rhinitis), fibrotic diseases and dermatosis (including psoriasis, atopic dermatitis and ultraviolet radiation (UV)-induced skin damage).

In another embodiment, the disorder mediated by inappropriate IKK2 activity is an inflammatory or tissue repair disorder. In another embodiment, the disorder mediated by inappropriate IKK2 activity is COPD, asthma or rhinitis. In another embodiment, the disorder mediated by inappropriate IKK2 activity is COPD. In another embodiment, the disorder mediated by inappropriate IKK2 activity is asthma. In a further embodiment, the disorder mediated by inappropriate IKK2 activity is rhinitis (including seasonal rhinitis, allergic rhinitis and vasomotor rhinitis).

In one embodiment, the present invention provides a method of treating asthma comprising administering a safe and effective amount of 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide or a pharmaceutically acceptable salt thereof to a human in need thereof.

In one embodiment, the present invention provides a method of treating COPD comprising administering a safe and effective amount of 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide or a pharmaceutically acceptable salt thereof to a human in need thereof.

The term "rhinitis" is used herein to refer to all types of rhinitis including allergic rhinitis such as seasonal rhinitis (for example hayfever) or perennial rhinitis, and non-allergic rhinitis or vasomotor rhinitis.

The invention also provides the compound of formula (I) or a pharmaceutically acceptable salt thereof for use in medical therapy, particularly in the treatment of disorders mediated by IKK2 activity. Thus, in a further aspect, the invention is directed to the use of the compound of formula (I), or a pharmaceutically acceptable salt thereof, in the manufacture of a medicament for use in the treatment of a disorder characterized by inappropriate IKK2 activity.

In one embodiment, the invention provides the compound of formula (I), or a pharmaceutically acceptable salt thereof, for use in the treatment of COPD (chronic obstructive pulmonary disease). In another embodiment, the invention provides the compound of formula (I), or a pharmaceutically acceptable salt thereof, for use in the treatment of asthma.

Compositions

The compound of formula (I), or a pharmaceutically acceptable salt thereof, will normally, but not necessarily, be formulated into pharmaceutical compositions prior to administration to a patient. Accordingly, in another aspect the invention is directed to pharmaceutical compositions comprising the compound of formula (I), or a pharmaceutically acceptable salt thereof, and one or more pharmaceutically acceptable excipients.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when co-mingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable eg of sufficiently high purity.

The compound of formula (I), or a pharmaceutically acceptable salt thereof, and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising the compound of formula (I), or a pharmaceutically acceptable salt thereof, and one or more pharmaceutically acceptable excipients which comprises mixing the ingredients. A pharmaceutical composition comprising the compound of formula (I), or a pharmaceutically acceptable salt thereof, may be prepared by, for example, admixture at ambient temperature and atmospheric pressure.

In another embodiment, the compounds of formula (I), or a pharmaceutically acceptable salt thereof, will be formulated for inhaled administration. For example, the compound of formula (I), or a pharmaceutically acceptable salt thereof, may be formulated as a dry powder, an aerosol, a suspension, or a solution composition.

Dry powder compositions for delivery to the lung by inhalation typically comprise the compound of formula (I), or a pharmaceutically acceptable salt thereof, as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of formula (I), or a pharmaceutically acceptable salt thereof.

Aerosols may be formed by suspending or dissolving the compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound of formula (I), or a pharmaceutically acceptable salt thereof, will typically be administered to a patient via a metered dose inhaler (MDI). Such devices are known to those skilled in the art.

The aerosol may contain additional pharmaceutically acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising the compound of formula (I), or a pharmaceutically acceptable salt thereof, and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of the compound of formula (I) or a pharmaceutically acceptable salt thereof and a suitable powder base such as lactose or starch. Each capsule or cartridge may generally contain from 20 μg to 10 mg of the compound of formula (I), or pharmaceutically acceptable salt thereof. Alternatively, the compound of formula (I), or pharmaceutically acceptable salt thereof, may be presented without excipients such as lactose.

The proportion of the active compound of formula (I), or pharmaceutically acceptable salt thereof, in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 µg to 10 mg, preferably from 20 µg to 2000 µg, more preferably from about 20 µg to 500 µg of the compound of formula (I). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and the compound of formula (I), or a pharmaceutically acceptable salt thereof, in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising the compound of formula (I), or a pharmaceutically acceptable salt thereof, may also be administered to a patient via a nebulizer. The solvent or suspension agent utilized for nebulization may be any pharmaceutically acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of formula (I), or pharmaceutically acceptable salt thereof, may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising the compound of formula (I), or a pharmaceutically acceptable salt thereof, together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising the compound of formula (I), or a pharmaceutically acceptable salt thereof, together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising the compound of formula (I), or a pharmaceutically acceptable salt thereof, together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I), or a pharmaceutically acceptable salt thereof, are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxoandrosta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compound of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (Sep. 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*, 10bS*)-9-ethoxy-1,2,3,4,4a,10b-hexahydro-8-methoxy-2-methylbenzo[c][1,6]naphthyridin-6-yl]-N,N-diisopropyl-benzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther,1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;

(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising the compound of formula (I), or a pharmaceutically acceptable salt thereof, together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising the compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

The invention thus provides, in a further aspect, a combination comprising the compound of formula (I), or a pharmaceutically acceptable salt thereof, together with a PDE4 inhibitor.

The invention thus provides, in a further aspect, a combination comprising the compound of formula (I), or a pharmaceutically acceptable salt thereof, together with a $\beta_2$-adrenoreceptor agonist.

The invention thus provides, in a further aspect, a combination comprising the compound of formula (I), or a pharmaceutically acceptable salt thereof, together with a corticosteroid.

The invention thus provides, in a further aspect, a combination comprising the compound of formula (I), or a pharmaceutically acceptable salt thereof, together with a non-steroidal GR agonist.

The invention thus provides, in a further aspect, a combination comprising the compound of formula (I), or a pharmaceutically acceptable salt thereof, together with an anticholinergic.

The invention thus provides, in a further aspect, a combination comprising the compound of formula (I), or a pharmaceutically acceptable salt thereof, together with an antihistamine.

The invention thus provides, in a further aspect, a combination comprising the compound of formula (I), or a pharmaceutically acceptable salt thereof, together with a PDE4 inhibitor and a $\beta_2$-adrenoreceptor agonist.

The invention thus provides, in a further aspect, a combination comprising the compound of formula (I), or a pharmaceutically acceptable salt thereof, together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of the compound of formula (I), or a pharmaceutically acceptable salt thereof, together with another therapeutically active agent.

The invention thus provides, in a further aspect, a pharmaceutical composition comprising a combination of the compound of formula (I), or a pharmaceutically acceptable salt thereof, together with a PDE4 inhibitor.

The invention thus provides, in a further aspect, a pharmaceutical composition comprising a combination of the compound of formula (I), or a pharmaceutically acceptable salt thereof, together with a $\beta_2$-adrenoreceptor agonist.

The invention thus provides, in a further aspect, a pharmaceutical composition comprising a combination of the compound of formula (I), or a pharmaceutically acceptable salt thereof, together with a corticosteroid.

The invention thus provides, in a further aspect, a pharmaceutical composition comprising a combination of the compound of formula (I), or a pharmaceutically acceptable salt thereof, together with a non-steroidal GR agonist.

The invention thus provides, in a further aspect, a pharmaceutical composition comprising a combination of the compound of formula (I), or a pharmaceutically acceptable salt thereof, together with an anticholinergic.

The invention thus provides, in a further aspect, a pharmaceutical composition comprising a combination of the compound of formula (I), or a pharmaceutically acceptable salt thereof, together with an antihistamine.

The invention thus provides, in a further aspect, a pharmaceutical composition comprising a combination of the compound of formula (I), or a pharmaceutically acceptable salt thereof, together with a PDE4 inhibitor and a $\beta_2$-adrenoreceptor agonist.

The invention thus provides, in a further aspect, a pharmaceutical composition comprising a combination of the compound of formula (I), or a pharmaceutically acceptable salt thereof, together with an anticholinergic and a PDE4 inhibitor.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in ° C. (degrees Centigrade). All reactions are conducted under an inert atmosphere at room temperature unless otherwise noted. All references to ether are to diethyl ether; brine refers to a saturated aq. solution of NaCl.

For a number of Intermediates and Example 3 the following abbreviations are used:
eq: equivalent (1 eq=1 mole reagent per 1 mole of starting material)
vol: volume (1 vol=1 ml per gram starting material)
wt: weight (1 wt=1 g reagent per 1 g starting material)
$^1$H NMR spectra were recorded using a Bruker DPX 400 MHz, referenced to tetramethylsilane.
LC/MS was conducted using the following method:
LC/MS (2 minute method) was conducted on a Acquity UPLC BEH $C_{18}$ column (5.0 cm×2.1 mm) at 40° C., eluting with 0.1% $HCO_2H$ and 0.01M ammonium acetate in water (solvent A) and 0.05% $HCO_2H$ 5% water in acetonitrile (solvent B), using the following elution gradient 0.0-0.1 min 3% B, 0.1-1.4 min 3-100% B, 1.4-1.9 min 100% B, 1.9-2 min 3% B at a flow rate of 1 ml/min. The mass spectra were recorded on a Waters ZQ Mass spectrometer using electrospray with pos negative switching (ES+ve and ES−ve).

In the LCMS data reported herein, the mass ion was mathematically rounded to the nearest integer.

LC (8 minute method) conditions:

| | |
|---|---|
| Analytical Column | Phenomenex Luna C18, 50 × 2.0 mm (i.d.) 3 µm |
| Mobile Phase | A = 0.05% TFA in water |
| | B = 0.05% TFA in acetonitrile |
| | 0-95% B over 8 minutes |
| Flow Rate | 1 mL/min |
| Temperature | 40° C. |
| Detection | UV, default 220 nm unless stated otherwise. |
| Injection Volume | 1 µL |
| Approximate Run Time | 8 mins |

"Hydrophobic frits" refers to filtration tubes sold by Whatman.

When the name of a commercial supplier is given after the name of a compound or a reagent, for instance "compound X (Aldrich)" or "compound X/Aldrich", this means that compound X is obtainable from a commercial supplier, such as the commercial supplier named.

The names of the Examples have been obtained from the structures using the compound naming programme "ACD Name Pro 6.02".

Intermediate 1:
5-Bromo-3-(4-piperidinyl)-1H-indole-7-carboxamide hydrochloride

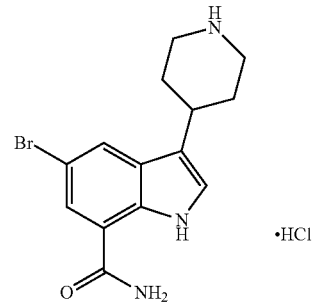 [SMILES: NC(=O)c1cc(Br)cc2c(C3CCNCC3)c[nH]c12 ; Cl]

1,1-Dimethylethyl-4-[7-(aminocarbonyl)-5-bromo-1H-indol-3-yl]-1-piperidinecarboxylate (which may be prepared according to WO2005067923A1, 74 g) was dissolved/suspended in methanol (300 mL) and to this was added 4N HCl in dioxane (200 mL). The reaction mixture was stirred for 2 hours. Diethyl ether (400 mL) was added and the solid was collected by filtration. This was washed with diethyl ether (300 mL) and dried in vacuo to give the title compound (66.53 g) as pale yellow solid.

LCMS (2 minute method) Rt=0.49 min; MH+=322/324.

Intermediate 1 (1st Alternative Preparation): 5-bromo-3-(4-piperidinyl)-1H-indole-7-carboxamide Method (850 g input):

Sodium borohydride (2.0 eq, 0.212 wt) was suspended in dry THF (10 vol) with stirring at 10-15° C. under nitrogen. Glacial acetic acid (2.0 eq, 0.321 vol) was then added dropwise over at least 15 mins at 10-25° C. at such a rate as to control effervescence (small exotherm, evolves hydrogen). Once the addition was complete, the resultant suspension was stirred for at least 15 mins under a flow of nitrogen until all visible effervescence has ceased. 5-bromo-3-(1,2,3,6-tetrahydro-4-pyridinyl)-1H-indole-7-carboxamide hydrochloride (which may be prepared, for example, by following the method outlined for Intermediate 8) (1 wt) was then added as a solid. The resultant suspension was then stirred at 20-25° C. under nitrogen for 3.5-4.5 hrs with HPLC monitoring. The batch was then cooled to 0-4° C. Hydrochloric acid (36% w/v, 0.90 vol) was then added in a dropwise manner over at least 30 mins maintaining the internal temperature at 0-4° C. throughout (exothermic, evolves hydrogen). The resultant slurry was stirred at 0-4° C. for 2 hrs, warmed to 20-25° C. and stirred for a further 2 hrs before recooling to 0-4° C. Water (8 vol) was then added slowly over at least 15 mins maintaining the internal temperature at 0-10° C. throughout (exothermic, evolves hydrogen). The resultant acidic solution was then stirred for at least 1 hr. A solution of aqueous sodium hydroxide (40% w/v, ca 2.5 vols) was added in a dropwise manner to neutralize to pH>12, maintaining the temperature at 0-15° C. throughout[1]. The resultant biphase was settled and separated. The aqueous was back-extracted with ethyl acetate (4 vols) and then discarded. The combined organics are washed with saturated brine (2×2 vols) before being concentrated in vacuo to ca 4 vols[2]. Ethyl acetate (8 vols) was added, and the batch was reconcentrated in vacuo to ca 4 vols. The resultant slurry was cooled to 0-5° C. and stirred for at least 30 mins. Solids are then collected by vacuum filtration and washed with ethyl acetate (2×1 vol). Dried in vacuo at 40-45° C. to constant weight.

LC (8 minute method) Rt=2.83 mins.

Yield: 79.6% theory, 72.0% w/w.

1 Max vol ca 23 vols

2 Min vol ca 4 vols

Intermediate 2: 5-Bromo-3-(1-{[2-(methyloxy)ethyl]sulfonyl}-4-piperidinyl)-1H-indole-7-carboxamide

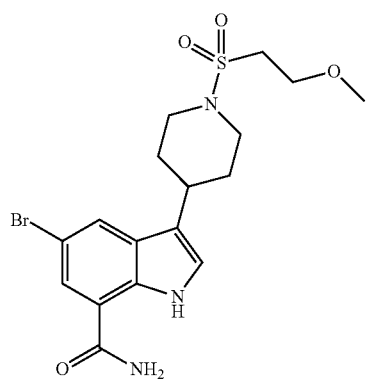 [SMILES: COCCS(=O)(=O)N1CCC(c2c[nH]c3c(C(N)=O)cc(Br)cc23)CC1]

Under nitrogen, 2-(methyloxy)ethanesulfonyl chloride (43.8 g) was added dropwise over 30 minutes to a cooled, 10° C., suspension of 5-bromo-3-(4-piperidinyl)-1H-indole-7-carboxamide hydrochloride (Intermediate 1, 66 g) in N,N-dimethylformamide (DMF) (350 mL) and triethylamine (77 mL). The reaction mixture was stirred for 3 hours. The reaction mixture was poured into water (2000 mL) and stirred for 1 hour. The resultant solid was collected by filtration and washed with water. The solid was dried in vacuo at 40° C. to give the title compound (67.1 g) as a cream solid.

LCMS (2 minute method) Rt=0.90 min; MH+=444/446.

Intermediate 2 (Ist Alternative Preparation): 5-bromo-3-(1-{[2-(methyloxy)ethyl]sulfonyl}-4-piperidinyl)-1H-indole-7-carboxamide Method (760 g input):

5-bromo-3-(4-piperidinyl)-1H-indole-7-carboxamide (which may be prepared, for example, by following the method outlined for Intermediate 1 (1st alternative preparation)) (1 wt) was suspended in THF (16 vol) and triethylamine (2.31 eq, 1.00 vol) was added. This stirred mixture was cooled to −5° C. under nitrogen. 2-(methyloxy)ethanesulfonyl chloride (which may be prepared, for example, by following the method outlined for Intermediate 4 (1st Alternative Preparation)) (1.6 eq, 0.788 wt) was added over at least 30 min, maintaining an internal temp of 0±5° C. The batch was then stirred for 2-3 hrs at 0±5° C. until complete by HPLC. The batch was then quenched with water (5 vols) and the resultant biphase[1] was settled and separated. The aqueous was discarded. The organics were washed with a 1:1 mixture of saturated brine and 2M aq HCl (2×2 vol) then saturated brine (2×2 vols). The organics were then concentrated in vacuo to ca 4 vols[2]. Ethyl acetate (8 vols) was added, and the batch was reconcentrated in vacuo to ca 4 vols. Ethyl acetate (4 vols) was added, and the batch was reconcentrated in vacuo to ca 4 vols. The resultant slurry was cooled to 0-5° C. and stirred for at least 30 mins. Solids are then collected by vacuum filtration and washed with ethyl acetate, (2×1 vol). Dried in vacuo at 40-45° C. to constant weight.

LC (8 minute method) Rt=4.59 mins.

Yield: 75.7% theory, 104.5% w/w.

1 Max vol ca 23 vols

2 Min vol ca 4 vols

Intermediate 3: Sodium 2-(methyloxy)ethanesulfonate

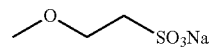

To a solution of 2-chloroethyl methyl ether (Acros, 68.0 mL) in 1,2-dimethoxyethane (DME) (250 mL) was added sodium sulfite (103 g) and water (250 mL). The reaction mixture was heated at reflux for 18 hours. The solvent was removed in vacuo and the residue was extracted with methanol (500 mL). The solid was removed by filtration and washed with methanol (250 mL). The combined filtrate and washings were evaporated in vacuo to give the title compound as a white solid.

$^1$H NMR (D6-DMSO): 3.54 (2H, m), 3.20 (3H, s), 2.69 (2H, m).

Intermediate 4: 2-(Methyloxy)ethanesulfonyl chloride

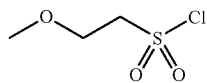

To sodium 2-(methyloxy)ethanesulfonate (Intermediate 3, 77 g) was added thionyl chloride (139 mL), followed by DMF (1.0 ml, 12.91 mmol) and the reaction mixture was heated at reflux under nitrogen for 18 hours. The thionyl chloride was removed on a rotory evaporator. The residue was separated between DCM (500 mL) and ice/water (300 mL). The organic phase was washed with brine (200 mL) and dried over magnesium sulphate. The organics were passed through an hydrophobic frit and the solvent removed in vacuo to give the title compound (62 g) as a colourless oil.

$^1$H NMR (CDCl$_3$): 3.97 (4H, m), 3.44 (3H, s)

Intermediate 4 (1st Alternative Preparation): 2-(methyloxy)ethanesulfonyl chloride Method (670 g input):

2-Methoxyethanol (1 wt, ≡1.038 vol) was dissolved in DCM (5 vol) and triethylamine (1.2 eq, 2.2 vol) was added. This mixture was cooled to 0° C. with stirring under nitrogen. Methanesulfonyl chloride (1.15 eq, 1.174 vol) was then added dropwise over 45-90 mins maintaining an internal temp below 10° C. At the end of the addition, the batch was stirred for 10-20 mins before water (5 vol) was added. The batch was vigorously stirred for 5-15 mins before being settled and separated. Aqueous discarded. The organic liquor was washed sequentially with 0.5M HCl (2 vol) and then 7% w/v aqueous sodium bicarbonate (2 vol) before being concentrated in vacuo to ca 2 vol$^2$. Water (7 vol) was added, followed by sodium thiosulfate pentahydrate (1.1 eq, 3.61 wt). This mixture was then heated to 80-85° C. and held thus for 2-2.5 hrs before cooling to 0-5° C. Diluted with acetic acid (7 vol) and readjusted to 0-5° C. Dichlorodimethylhydantoin (2.2 eq, 5.66 wt) was added in 6 portions at 10-15 minute intervals, maintaining the internal temperature below 25° C. Batch then adjusted to 25° C. and stirred at 23-28° C. for 2-2.5 hrs. DCM (11 vol) was then added and the batch was stirred vigorously for 5-15 mins to obtain a complete biphasic solution$^1$. This was settled and separated, and the aqueous was back-extracted with DCM (4 vol) before being discarded. The combined organic liquors were washed with water (2×7 vol) before being chilled to 0-5° C. A solution of aqueous sodium metabisulfate (5% w/v, 12 vol) was then added dropwise over 15-30 mins with vigorous stirring, maintaining an internal temperature below 25° C. Stirred for a further 5-15 mins, then the biphase was settled and separated.

The organic liquor was then sequentially washed with 5% w/v aqueous sodium metabisulfite (2×5 vol) and then water (5 vol) before being concentrated in vacuo to ca 2 vol$^2$.

Yield: 77% theory, 160% w/w corrected for DCM content.
1: Maximum volume of ca 32 vols is achieved at this point.
2: Minimum volume of ca 2 vols is achieved at these points.

Intermediate 5: 5-Bromo-2-(1-methylethyl)-1H-isoindole-1,3(2H)-dione

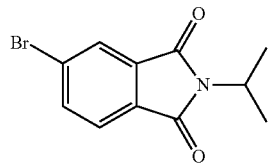

To a suspension of 5-bromo-1H-isoindole-1,3(2H)-dione (ABCR, 5.0 g) and triphenylphosphine (8.70 g) in tetrahydrofuran (THF) (100 mL) under nitrogen at room temperature was added di-t-butyl azodicarboxylate (7.64 g). The suspension was cooled in an ice/water bath and to this was added iso-propanol (2.032 mL). The reaction mixture was allowed to warm to room temperature to give a pale yellow solution. After 60 minutes, the solvent was removed in vacuo and the residue was dissolved in DCM (30 mL). This was applied to a 750 g silica cartridge and eluted with a gradient of 0-40% ethyl acetate in cyclohexane over 8CV. The required fractions were combined and evaporated in vacuo to give the title compound (5.27 g) as a pale yellow solid.

$^1$H NMR (CDCl$_3$): 7.95 (1H, d, J=1.5 Hz), 7.84 (1H, dd, J=1.5, 8 Hz), 7.68 (1H, d, J=8 Hz), 4.53 (1H, heptet, J=7 Hz), 1.49 (6H, d, J=7 Hz)

Intermediate 6: 5-Bromo-2-(1-methylethyl)-2,3-dihydro-1H-isoindole

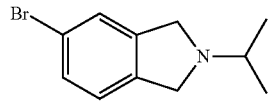

To a solution of 5-bromo-2-(1-methylethyl)-1H-isoindole-1,3(2H)-dione (Intermediate 5, 4.27 g) in tetrahydrofuran (THF) (100 mL) under nitrogen at room temperature was added 1.0M borane-tetrahydrofuran complex in THF (80 mL). The reaction mixture was heated at reflux for 48 hours. More 1.0M borane-THF complex in THF (50 mL) was added and the reaction mixture was heated at reflux for a further 24 hours. The reaction mixture was allowed to cool to room temperature. The reaction was quenched by the dropwise addition of 2N hydrochloric acid (80 mL). The reaction mixture was then heated at reflux for 1 hour. The reaction mixture was separated between ethyl acetate (300 mL) and water (50 mL). The organic phase was washed with 2N hydrochloric acid (100 mL). The combined aqueous phases were basified using 2N sodium hydroxide solution and then extracted with ethyl acetate (300 mL). This organic phase was washed with brine (100 mL) and dried over magnesium sulphate. The solvent was evaporated in vacuo to give the title compound (3.0 g) as a white solid.

LCMS (2 minute method) Rt=0.49; MH$^+$=240/244

Intermediate 7: [2-(1-Methylethyl)-2,3-dihydro-1H-isoindol-5-yl]boronic acid

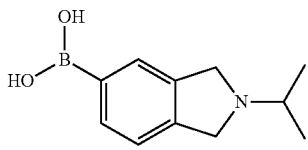

A solution of 5-bromo-2-(1-methylethyl)-2,3-dihydro-1H-isoindole (Intermediate 6, 20 g) in dry tetrahydrofuran (THF) (200 mL) was added to magnesium turnings (3.04 g). To this was added a crystal of iodine and the reaction mixture was heated at reflux for 4 hours. The reaction mixture was cooled to 5° C. and to this was added trimethyl borate (11.17 mL). After 1 hour the reaction was quenched with 2N hydrochloric acid (200 mL). The aqueous phase was extracted with ethyl acetate (3×200 mL), with each extraction was added triethylamine (50 mL). The combined organics were dried over magnesium sulphate and evaporated in vacuo to give a brown foam. This was triturated with TBME (300 mL) and the solid was collected by filtration to give the title compound (9.0 g) as an off-white solid.

LCMS (2 minute method) Rt=0.33; MH$^+$=206

Intermediate 8: 5-bromo-3-(1,2,3,6-tetrahydro-4-pyridinyl)-1H-indole-7-carboxamide hydrochloride

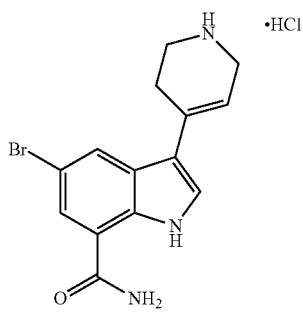 [SMILES: Cl ; NC(=O)c1cc(Br)cc2c(C3=CCNCC3)c[nH]c12]

Method (1300 g input):

5-bromo-1H-indole-7-carboxamide (which may be prepared according to Intermediate 7, WO2005067923) (1 wt), 1,1-dimethylethyl 4-oxo-1-piperidinecarboxylate (1.20 wt, 1.5 eq) and sulfamic acid (0.5 eq, 0.2031 wt) were all charged sequentially to an empty reactor. Acetic acid (5 vols) was added and the mixture was heated to 70-74° C. Held thus with stirring under nitrogen for 15-25 hrs until the level of 5-bromo-1H-indole-7-carboxamide by HPLC is <5% a/a uncorrected. A mixture of hydrochloric acid (36%, 0.52 vol, 1.5 eq) and acetic acid (0.5 vol) was prepared. This mixture was then added drop-wise to the batch over ca 30 mins, maintaining an internal temp of 65-74° C. The batch was stirred for a further 30 mins at 65-74° C. before warming to 93-97° C. Stirred within this temp range under nitrogen for 15-25 hrs, until the 2:1 dimer impurity (rrt 1.15 on 8 min reverse phase LC method) is <10% a/a uncorrected. Batch then cooled back to 15-25° C. and aged within this temp range for at least 60 mins. Product then collected by vacuum filtration and washed with IMS (2×2 vol). Dried to constant weight at 40° C. in vacuo.

LC (8 minute method) Rt=2.76 mins.
Yield=80% theory, 119% w/w

Intermediate 9: 3-(1-{[2-(methyloxy)ethyl]sulfonyl}-4-piperidinyl)-5-(4,4,5,5,-tetramethyl-1,3,2-dioxaborolan-2-yl)-1H-indole-7-carboxamide

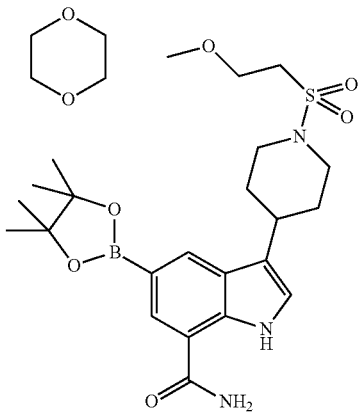 [SMILES: COCCS(=O)(=O)N1CCC(c2c[nH]c3c(C(N)=O)cc(B4OC(C)(C)C(C)(C)O4)cc23)CC1 ; C1COCCO1]

Method (137 g input):

5-bromo-3-(1-{[2-(methyloxy)ethyl]sulfonyl}-4-piperidinyl)-1H-indole-7-carboxamide (which may be prepared, for example, by following the method outlined for Intermediate 2 (1$^{st}$ Alternative preparation) (1 wt) was suspended in dioxan (6 vol) with stirring under nitrogen$^2$. 4,4,4',4',5,5,5',5'-octamethyl-2,2'-bi-1,3,2-dioxaborolane (1.05 eq, 0.600 wt) was added, followed sequentially by potassium acetate (2.5 eq, 0.553 wt), palladium (II) acetate (0.01 eq, 0.00505 wt), and X-Phos (0.03 eq, 0.0321 wt). The resultant suspension was heated to 99-101° C. with stirring under nitrogen and held thus with periodic monitoring by HPLC. Reaction typically takes 3-5 hrs to reduce starting material to <1% a/a. The batch was then cooled to 80-85° C. and water (6 vol) was added at such a rate as to maintain the internal temp above 80° C.$^1$. Product crystallization is expected during or immediately after the addition. Once crystallization was established, the batch was further cooled to 18-23° C. and aged for a minimum of 30 mins within this temperature range. Product was collected by vacuum filtration, and the solids were sequentially washed with 1:1 aqueous dioxan (2×2 vol) and then water (2×2 vol). The batch was then dried in vacuo at 40-45° C. to constant weight.

LC (8 minute method) Rt=5.00 mins.
Yield: 83.2% theory, 108% w/w.

1 A maximum volume of ca 13 vols is achieved at this point.
2 A minimum volume of ca 6.5 vols is achieved at this point.

Intermediate 10: 5-bromo-2-(1-methylethyl)-2,3-dihydro-1H-isoindole hydrochloride

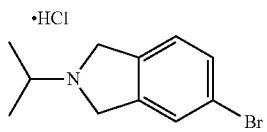

Method (625 g input):

5-bromo-2-benzofuran-1,3-dione (1 wt) was suspended in toluene (5 vol) with stirring under nitrogen. Isopropylamine (1.1 eq, 0.416 vol) was then added dropwise over 10-30 mins at such a rate as to maintain the temperature between 15-25° C. (exothermic addition). The batch was stirred for a further 30 mins at 15-25° C. once the addition was complete, before heating to reflux under Dean-Stark conditions. The batch was held at reflux for 5-8 hrs until residual 5-bromo-2-benzofuran-1,3-dione by HPLC is <1% a/a uncorrected, then the batch was concentrated atmospherically to ca 2.5 vols[2]. Added toluene (3 vols) and reconcentrated atmospherically to ca 2.5 vols. Batch then cooled to 55-60° C., diluted with THF (1.5 vols), and then further cooled to 15-25° C. This was added to a solution of borane-THF complex (1.0M, 4 eq, 14.1 vol) and the resultant solution was stirred at 20-30° C. for ca 30 mins. The batch was then heated to 48-52° C., and held thus for 16-24 hrs until complete by HPLC, before cooling back to 15-25° C. The reaction was quenched inversely into aqueous hydrochloric acid (2N, 9 vol) over at least 30 mins maintaining an internal temp of 15-30° C. (initially effervescent, evolves hydrogen). Once the addition was complete, the batch was heated to 60-63° C., and held thus for 1-1.5 hrs before cooling to 15-25° C. Ethyl acetate (6 vols) was added and the resultant biphase was shaken, settled and separated[1]. Organics back-extracted with 2N HCl (3 vols) before being discarded. The combined aqueous liquors were then neutralized to pH>12 with 40% w/v aq NaOH (approx 3.9 vols). Overlain with ethyl acetate (6 vols) then the resultant biphase was shaken, settled and separated. Aqueous back extracted with ethyl acetate (3 vols) before being discarded. The organics were combined and washed with saturated brine (2×2 vols) before being concentrated in vacuo to ca 4 vols. Ethyl acetate (8 vols) was added and the batch was reconcentrated in vacuo to ca 4 vols. Ethyl acetate (9 vols) was added and the batch was adjusted to 0±3° C. 4M HCl in dioxane (0.89 eq, 0.98 vol) was then added slowly maintaining the batch temp within the range 0±3° C. The batch was then aged within this range for 30 min before product was collected by vacuum filtration. Washed with chilled ethyl acetate (<5° C., 2×2 vols) and dried o/n in vacuo at 30° C. to constant weight.

LC (8 minute method) Rt=2.75 mins.

Yield: 82.0% theory, 99.9% w/w.

1 A maximum volume of ca 33 vols occurs here
2 A minimum volume of ca 2.5 vols occurs here Example 1

Compound of formula (I): 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide

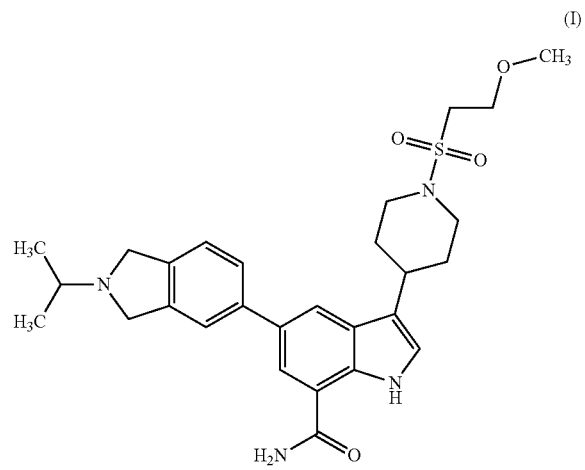 [SMILES: COCCS(=O)(=O)N1CCC(c2c[nH]c3c(C(N)=O)cc(-c4ccc5c(c4)CN(C(C)C)C5)cc23)CC1]

A suspension of 5-bromo-3-(1-{[2-(methyloxy)ethyl]sulfonyl}-4-piperidinyl)-1H-indole-7-carboxamide (Intermediate 2, 15 g), [2-(1-methylethyl)-2,3-dihydro-1H-isoindol-5-yl]boronic acid (Intermediate 7, 11.08 g) and potassium carbonate (14 g) in 1,4-dioxane (150 mL) and water (30 mL) was degassed. To this was added $PdCl_2(dppf)\cdot CH_2Cl_2$ adduct (1.378 g) and the reaction mixture was heated at 90° C. for 1.5 hours. The reaction mixture was allowed to cool to room temperature. The reaction mixture was separated between ethyl acetate and 2N hydrochloric acid. The aqueous phase was washed with ethyl acetate. The aqueous phase was basified using solid potassium carbonate and then extracted with ethyl acetate. The ethyl acetate extract was dried over magnesium sulphate. The solvent was removed in vacuo and the residue was dissolved in DCM. This was applied to a 340 g silica cartridge and eluted with a gradient of 0-30% methanol in DCM over 12CV. This gave two batches of a tan foam.

The two batches were each dissolved in DMSO/methanol (20 mL, 1:1 v/v) and applied to two 340 g C18 silica cartridges. These were eluted using a gradient of 10-95% acetonitrile in water (+0.1% TFA) over 8CV. The required fractions from both columns were combined and the acetontrile was removed on a rotory evaporator. The resultant aqueous phase was basified using saturated sodium bicarbonate solution. This was extracted using ethyl acetate. The organic phase was dried over magnesium sulphate and evaporated in vacuo. The resultant foam was triturated with TBME (100 mL). The solid was collected by filtration, washed with TBME and dried in vacuo to give the title compound (7.25 g) as a white solid.

LCMS (2 minute method) $MH^+$=525, Rt=0.68 min; $^1H$ NMR (DMSO-$d_6$) d: 10.89 (d, J=2.5 Hz, 1H), 8.20 (br. s., 1H), 7.99 (d, J=1.5 Hz, 1H), 7.98 (d, J=1.5 Hz, 1H), 7.65 (s, 1H), 7.61 (dd, J=8.0, 1.5 Hz, 1H), 7.37 (br. s., 1H), 7.32 (d, J=8.0 Hz, 1H), 7.15 (d, J=2.5 Hz, 1H), 3.95 (s, 2H), 3.91 (s, 2H), 3.66-3.73 (m, 2H), 3.69 (t, J=6.0 Hz, 2H), 3.34 (t, J=6.0 Hz, 2H), 3.30 (s, 3H), 2.98-3.07 (m, 1H), 2.95-3.04 (m, 2H), 2.73 (spt, J=6.0 Hz, 1H), 2.04-2.12 (m, 2H), 1.67 (qd, J=12.5, 4.0 Hz, 2H), 1.13 (d, J=6.0 Hz, 6H).

The title compound was characterised as follows:

X-Ray Powder Diffraction (XRPD)

XRPD data were acquired on a PANalytical X'Pert Pro powder diffractometer, equipped with an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ. The time per step was 31.750 s. The sample was prepared by mounting a few milligrams of sample on a Si wafer (zero background) plate, resulting in a thin layer of powder.

The XRPD pattern is shown in FIG. 1. Characteristic XRPD angles and d-spacings are recorded in the Table 1 below. The margin of error is approximately ±0.1° 2θ for each of the peak assignments. Peak positions were measured using Highscore software.

TABLE 1

| Position 2θ/° (±0.1° 2θ) | d-spacing/Å |
|---|---|
| 6.4 | 13.8 |
| 7.4 | 12.0 |
| 7.9 | 11.1 |
| 9.6 | 9.2 |
| 11.0 | 8.0 |
| 11.3 | 7.8 |
| 12.0 | 7.4 |
| 12.4 | 7.1 |
| 15.3 | 5.8 |
| 15.6 | 5.7 |
| 16.7 | 5.3 |
| 17.4 | 5.1 |
| 18.5 | 4.8 |
| 19.7 | 4.5 |
| 20.5 | 4.3 |
| 21.8 | 4.1 |

TABLE 1-continued

| Position 2θ/° (±0.1° 2θ) | d-spacing/Å |
|---|---|
| 22.1 | 4.0 |
| 23.9 | 3.7 |
| 25.8 | 3.5 |
| 26.9 | 3.3 |

Differential Scanning Calorimetry (DSC)

The DSC thermogram was obtained using a Perkin Elmer Pyris 1 calorimeter, and the data processed using TA Universal Analysis software. The sample was weighed and sealed in vented aluminium pan. The experiment was conducted using a heating rate of 10° C. min$^{-1}$. The DSC thermogram of the product from Example 1 is shown in FIG. 2.

A melt with combined degredation with an onset temperature of about 115° C. was observed.

Example 2

5-[2-(1-methylethyl)-2,3-dihydro-1H-isoindol-5-yl]-3-(1-{[2-(methyloxy)ethyl]sulfonyl}-4-piperidinyl)-1)-1H-indole-7-carboxamide trifluoroacetate To a solution of 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide (Example 1, 213 mg) in methanol (20 mL) was added trifluoroacetic acid (0.034 mL). The solvent was removed in vacuo and the residue was triturated with t-butyl methyl ether (10 mL). The solid was collected by filtration and dried in vacuo to give the title compound (194mg) as an off-white solid.

$^1$H NMR (DMSO-d$_6$) d: 10.96 (d, J=2.0 Hz, 1H), 10.74-10.82 (m, 1H), 8.22 (br. s., 1H), 8.03 (s, 1H), 8.01 (s, 1H), 7.81-7.86 (m, 2H), 7.49 (d, J=8.0 Hz, 1H), 7.43 (br. s., 1H), 7.18 (d, J=2.0 Hz, 1H), 4.83 (dd, J=14.0, 5.0 Hz, 2H), 4.64 (td, J=14.0, 7.0 Hz, 2H), 3.73-3.82 (m, 1H), 3.71-3.75 (m, 2H), 3.70 (t, J=6.0 Hz, 2H), 3.35 (t, J=6.0 Hz, 2H), 3.30 (s, 3H), 2.98-3.07 (m, 1H), 2.99 (td, J=12.5, 2.0 Hz, 2H), 2.04-2.11 (m, 2H), 1.69 (qd, J=12.5, 4.0 Hz, 2H), 1.37 (d, J=6.0 Hz, 6H).

Example 3

Compound of formula (I): 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide

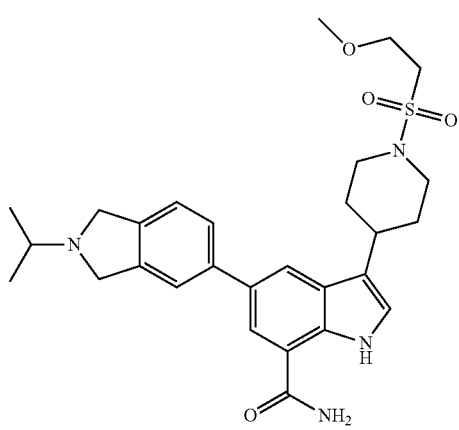 [SMILES: COCCS(=O)(=O)N1CCC(c2c[nH]c3c(C(N)=O)cc(-c4ccc5c(c4)CN(C(C)C)C5)cc23)CC1]

Method:

A suspension of 5-bromo-2-(1-methylethyl)-2,3-dihydro-1H-isoindole hydrochloride (which may be prepared, for example, by following the method outlined for Intermediate 10) (1.05 eq) and potassium phosphate tribasic monohydrate (3 eq) in dioxane (7.5 vol) and water (2.5 vol) was stirred for 15 min to give a solution. To this solution was added 3-(1-{[2-(methyloxy)ethyl]sulfonyl}-4-piperidinyl)-5-(4,4,5,5-tetramethyl-1,3,2-dioxaborolan-2-yl)-1H-indole-7-carboxamide (which may be prepared, for example, by following the method outlined for Intermediate 9) (1.0 eq), Pd$_2$dba$_3$ (0.005 eq) and XPhos (0.02 eq). The resulting mixture was heated to just below reflux (85-87° C.) and stirred at that temperature for 2.5 hrs until complete by HPLC (<2.5% a/a 3-(1-{[2-(methyloxy)ethyl]sulfonyl}-4-piperidinyl)-5-(4,4,5,5-tetramethyl-1,3,2-dioxaborolan-2-yl)-1H-indole-7-carboxamide+boronic acid). The biphasic mixture was cooled to 60 C and the aqueous phase removed. To the organic phase was added water (2 vol) and the solution stirred for 1 h. The resultant black precipitate was removed by filtration through a 1.0 micron followed by a 0.2 micron filter. The filtrate is reheated to 60 C and water (10-11.5 vol—to give a total of 12.5 vol) is added over 30 min whilst maintaining an internal temperature between 50 and 60 C. The resultant slurry was cooled to 20 C over 1 h and aged at 20 C for 1 h and the solid collected by filtration. The cake was washed with a mixture of dioxane and water (3:5, 2×2 vol) and water (2 vol). To a slurry of the damp cake in a mixture of 2-MeTHF (6 vol) and water (6 vol) is added citric acid (1.1 eq). The mixture is stirred to achieve dissolution. The aqueous phase is separated and washed with 2-MeTHF (6 vol). To the aqueous phase at ambient temp is added methanol (2 vol) followed by a 2N NaOH solution (2 vol) dropwise over 30 min. The mixture is stirred at ambient temp for 1 h and the solid collected by filtration. The cake is washed with water (2×2 vol) and dried o/n at 40 C under vacuum.

LC (8 minute method) Rt=3.55 mins.

Figure 3:
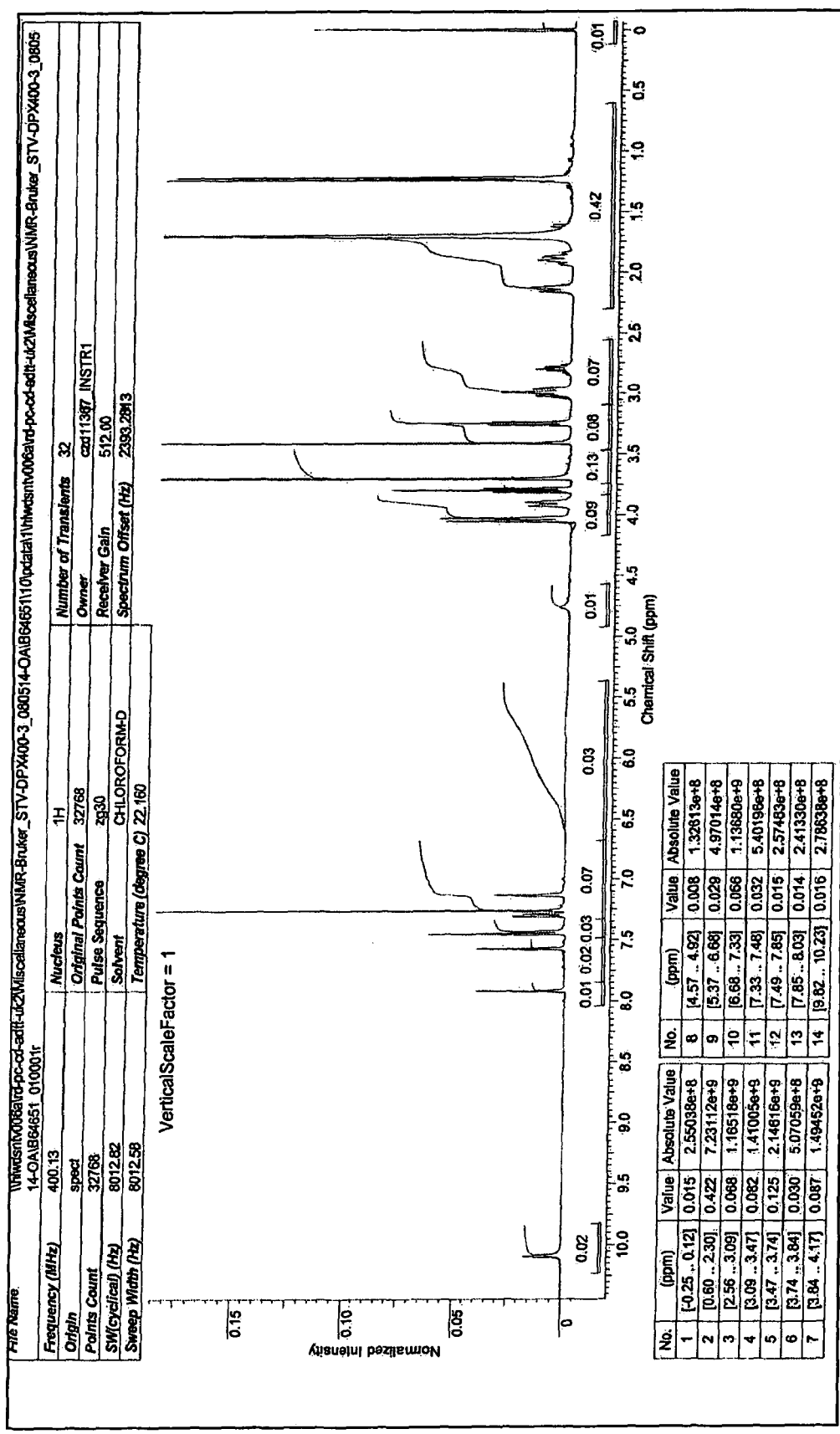
FIG. 3 shows the Proton NMR spectrum of Example 3.

The proton NMR spectrum recorded for this Intermediate is shown in FIG. 3.

Yield: >70% theory

Biological Data

1. In Vitro Data

IKK2 Assay

Recombinant human IKKβ (residues 5-756) was expressed in baculovirus as a C-terminal GST-tagged fusion protein, and its activity was assessed using a time-resolved fluorescence resonance energy transfer (TR-FRET) assay. Briefly, IKKβ (0.5-4 nM final concentration) diluted in assay buffer (50 mM HEPES, 10 mM MgCl$_2$, 1 mM CHAPS pH 7.4 with 1 mM DTT and 0.01% w/v BSA) was added to wells containing various concentrations of compound or DMSO vehicle (1.7% v/v final). The reaction was initiated by the addition of GST-IkappaBalpha substrate (25 nM final)/ATP (1 μM final), in a total volume of 6 μl. The reaction was incubated for 15 mins at room temperature, then terminated by the addition of 3 μl of 50 mM EDTA in buffer (100 mM HEPES pH 7.4, 150 mM NaCl and 0.1% w/v BSA) containing antiphosphoserine-IkappaBalpha-32/36 monoclonal antibody clone 12C2 (Cell Signalling Technology, Beverly Mass., USA) labelled with W-1024 europium chelate (Wallac OY, Turku, Finland), and an APC-labelled anti-GST antibody (Prozyme, San Leandro, Calif., USA). The reaction was further incubated for 60 mins at room temperature and the degree of phosphorylation of GST-IkappaBalpha measured using a Rubystar plate reader (BMG Instruments, Aylesbury, UK) as a ratio of specific 665 nm energy transfer signal to reference europium 620 nm signal.

IKK2 Time Dependent Assay

Recombinant human IKKβ (residues 5-756) was expressed in baculovirus as a C-terminal GST-tagged fusion protein, and its activity was assessed using a time-resolved fluorescence resonance energy transfer (TR-FRET) assay. Briefly, IKKβ (0.5-4 nM final concentration) diluted in assay buffer (50 mM HEPES, 10 mM $MgCl_2$, 1 mM CHAPS pH 7.4 with 1 mM DTT and 0.01% w/v BSA) was added to wells containing various concentrations of compound or DMSO vehicle (1.7% v/v final). Enzyme and compound were incubated for 60 mins at room temperature prior to addition of ATP and IkappaBalpha substrate. The reaction was initiated by the addition of GST-IkappaBalpha substrate (25 nM final)/ATP (1 µM final), in a total volume of 6 µl. The reaction was incubated for 15 mins at room temperature, then terminated by the addition of 3 µl of 50 mM EDTA in buffer (100 mM HEPES pH 7.4, 150 mM NaCl and 0.01% w/v BSA) containing antiphosphoserine-IkappaBalpha-32/36 monoclonal antibody clone 12C2 (Cell Signalling Technology, Beverly Mass., USA) labelled with W-1024 europium chelate (Wallac O Y, Turku, Finland), and an APC-labelled anti-GST antibody (Prozyme, San Leandro, Calif., USA). The reaction was further incubated for 30 mins at room temperature and the degree of phosphorylation of GST-IkappaBalpha measured using a Packard Discovery (Perkin-Elmer Life Sciences, Pangbourne, Berkshire, UK), Wallac Viewlux (Perkin-Elmer Life Sciences, Pangbourne, Berkshire, UK), Envision (Perkin-Elmer Life Sciences, Pangbourne, Berkshire, UK), or Rubystar (BMG, Aylesbury, Buckinghamshire, UK) as a ratio of specific 665 nm energy transfer signal to reference europium 620 nm signal.

IKK1 Time-Resolved Fluorescence Resonance Energy Transfer Assay

Recombinant human IKK1 (residues 1-785) was expressed in baculovirus as a C-terminal 6HIS-tagged fusion protein, and its activity was assessed using a time-resolved fluorescence resonance energy transfer (TR-FRET) assay. Briefly, IKK1 (typically 5-10 nM final) diluted in assay buffer (50 mM HEPES, 10 mM $MgCl_2$, 1 mM CHAPS pH 7.4 with 1 mM DTT and 0.01% w/v BSA) was added to wells containing various concentrations of compound or DMSO vehicle (1.7% v/v final). The reaction was initiated by the addition of GST-IκBα substrate (25 nM final)/ATP (1 µM final), in a total volume of 6 µl. The reaction was incubated for 15 minutes at room temperature, then terminated by the addition of stop reagent (3 µl) containing 50 mM EDTA and detection reagents in buffer (100 mM HEPES pH 7.4, 150 mM NaCl and 0.01% w/v BSA). Detection reagents comprise antiphosphoserine-IκBα-32/36 monoclonal antibody 12C2 (Cell Signalling Technology, Beverly Mass., USA) labelled with W-1024 europium chelate (Wallac O Y, Turku, Finland) and an allophycocyanin-labelled anti-GST antibody (Prozyme, San Leandro, Calif., USA). The reaction mixture (9 µl total volume) was further incubated for at least 45 minutes at room temperature. The degree of phosphorylation of GST-IκBα was measured using a suitable time-resolved fluorimeter such as Packard Discovery (Perkin-Elmer Life Sciences, Pangbourne, Berkshire, UK), Wallac Viewlux (Perkin-Elmer Life Sciences, Pangbourne, Berkshire, UK), Envision (Perkin-Elmer Life Sciences, Pangbourne, Berkshire, UK), or Rubystar (BMG, Aylesbury, Buckinghamshire, UK) as a ratio of specific 665 nm energy transfer signal to reference europium 620 nm signal.

Human Peripheral Blood Mononuclear Cell Assay and Human Whole Blood Assay

Human Peripheral Blood Mononuclear Cell Assay

The cellular potency of compounds was assessed in human peripheral blood mononuclear cells (PBMC) by measuring their impact on lipopolysaccharide (LPS) stimulated TNFα production. PBMCs were prepared from heparinised human blood from normal volunteers by centrifugation on hystopaque in Accuspin tubes at 800 g for 20 minutes. The cells were collected from the interface, washed by centrifugation (1300 g, 10 minutes) and resuspended in assay buffer (RPMI1640 containing 10% foetal calf serum, 1% L-glutamine and 1% penicillin/streptomycin) at $1\times10^6$ cells/ml. 50 µl cells were added to microtitre wells containing 1.0 µl of an appropriately diluted compound solution which had been solvated and diluted in DMSO. 75 µl LPS (s. typhosa Sigma Cat L6386, 1 ng/ml final) was added and the samples incubated at 37° C., 5% $CO_2$ for 20 hours. The supernatant was removed and the concentrations of TNF determined by electrochemiluminescence assay using the MSD technology.

Human Whole Blood Assay

Heparinised blood drawn from normal volunteers was dispensed (100 µl) into microtitre plate wells containing 1.0 µl of an appropriately diluted compound solution in DMSO. After 1 hr incubation at 37° C., 5% $CO_2$, 25 µl LPS solution (S. typhosa) in RPMI 1640 (containing 1% L-glutamine and 1% Penicillin/streptomycin) was added (50 ng/ml final). The samples were incubated at 37° C., 5% $CO_2$ for 20 hours, 50 µls physiological saline (0.138% NaCl) was added and diluted plasma was collected using a Biomek FX liquid handling robot after centrifugation at 1300 g for 10 min. Plasma TNFα content was determined by electrochemiluminescence assay using the Mesoscale (MSD) technology.

TNFα Assay associated with PBMC and Whole Blood Assays

20 µl supernatant from PBMC plates or 40 µl from whole blood plates was transferred using the Biomek FX to a 96 well High-Bind MSD assay plate precoated with anti-hTNF alpha capture antibody and containing 25 µl of MSD human serum cytokine assay diluent. Each plate also contained a TNFα standard curve (0-5000 pg/ml: R+D Systems, 210-TA). For the Whole blood assay, plates were sealed and shaken for 2 hours at room temperature after which they were washed and 40 µl of MSD detection antibody was added. The plates were shaken at room temperature for a further 1 hour before washing again and adding 150 µl of MSD Read Buffer T (2×). Plates were then read on the MSD Sector 6000 plate reader. For the PBMC assay, supernatant addition to the MSD plates was followed immediately by 20 µl of MSD detection antibody, the plates were then sealed and shaken for 2 hours before addition of 90 µl of MSD Read Buffer P (2.5×). Plates were read on the MSD Sector 6000.

TNF concentrations were derived from the standard curve run on the same plate and pIC50 values for inhibition of TNF production were derived from the compound dose response curves with non-linear least squares curve fitting using Activity base software.

NFkB Reporter Assay

A 70% confluent T225 flask of A549 SPAP cells was harvested by centrifugation for 5 min at 200 g, resuspended in assay buffer (DMEM supplemented with 10% FCS 2×HI, 2 mM L-Glutamine, 1% Pen/Strep and Non essential amino acids) and diluted to $0.16\times10^6$/ml. 60 µl of cell solution was dispensed to each well of clear Nunc 384-well plates, containing 0.5 µl compound in neat DMSO at 140× the required final assay concentration. Plates were incubated for 1h at 37° C., 95% humidity, 5% CO2 before 10 ml of TNF solution in assay buffer was added to give a final concentration of 3.2 ng/ml and then returned to the cell incubator for 15 h. Plates were equilibrated to room temperature for 1 h prior to the addition of 25 µl of pNPP buffer (1 M Diethanolamine pH 9.8, 0.5 mM $MgCl_2$, 0.28M NaCl, 2 mg/ml pNPP) to each well of assay plates. The plates were covered to protect the reagents from light, and then incubated at room temperature for approximately 1 hour before reading them on an Ascent using a 405 nm single filter.

All data was normalized to the mean of 16 high and 16 low control wells on each plate. A four parameter curve fit of the following form was then applied

2. In Vivo Data

Inhaled LPS Induced Neutrophilia in the Male CD Rat
Compound/Vehicle Pretreatment Male CD rats (150-250 g) were anaesthetised with isoflurane (5%, 2 L/min $O_2$, 1 L/min NO) and positioned on their back on a dosing table at a 35 degree angle, with a metal rod placed under their incisors to keep them in place. A light was angled against the outside of the throat to highlight the trachea. The mouth was opened to visualise the upper opening of the airway and a portex cannula was introduced into the trachea via a blunt dosing needle. 200 ul of compound formulation was then injected into the airways. After dosing, animals were placed in a supine position during recovery from anaesthesia.

LPS Challenge Protocol

Approximately thirty minutes following dosing of compound or vehicle, the rats were placed into a cloud chamber and exposed to an aerosol of lipopolysaccharide, generated from a 150 ug/ml solution for 15 min.

Lung Lavage Protocol

Four hours following LPS challenge the animals were culled with an overdose of sodium pentobarbitone given intraperitoneally. The trachea was exposed and a small incision made, into which a tube was inserted towards the lungs. The lungs were then washed with 3 times with 5 mls heparinised (10 U/ml) PBS.

Cell Counts

The bronchoalveolar lavage fluid (BALF) samples were centrifuged at 1300 rpm for 7 minutes. The supernatant was removed and the resulting cell pellet resuspended in 0.5 ml PBS. A cell slide of the resuspension fluid was prepared by placing 75 l of resuspended BALF fluid into cytospin holders and then spun at 500 rpm for 5 minutes. The slides were allowed to air dry and then stained with Leishmans stain (20 minutes) to allow differential cell counting. The total cells were also counted from the resuspension using a Sysmex counter. From these two counts, the total numbers of neutrophils in the BALF were determined.

Bone Marrow Micronucleus Assay in Rats

Objective

The objective of this study was to assess the potential of 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide in induce structural chromosomal damage and/or aneuploidy in vivo, in polychromatic erythrocytes from rat bone marrow, when administered to rats for two consecutive days.

Crl: CD(SD) rats were used in this study.

Animals were dosed orally, at a dose volume of 10 mL/kg, as this route was shown to achieve higher bioavailability and systemic exposure than by the inhaled route.

Dose Range Finding Test

Doses of 500, 1000, 2000 mg/kg/day of 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide, or vehicle (0.5% (w/v) aqueous hydroxypropylmethylcellulose containing 0.1% (w/v) Tween 80), were given orally (by gavage) to groups of 3 male and 3 female rats. All rats were killed 24 hours after receiving their final dose and femoral bone marrow spears prepared. Smears stained with acridine orange prior to analysis with fluorescense microscopy to determine the proportion of polychromatic erythrocytes in the total erythrocyte count (% PCE). Additionally, analysis of plasma samples from groups of 3 male and 3 female satellite bioanalysis animals dosed once at 500, 1000 or 2000 mg/kg/day and sampled 4 hours after dosing, was conducted to confirm in vivo exposure to 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide. Dose selection for the main micronucleus assay was based on the results of the dose range finder.

As there were no apparent gender differences in systemic toxicity, systemic exposure or group mean % PCE in the dose range finding text, only male animals were used in the main micronucleus test.

Micronucleus Assay

Doses of 1000 or 2000 mg/kg/day 5-[2-(1-methylethyl)-2,3-dihydro-1H-isoindol-5-yl]-3-(1-{[2-(methyloxy)ethyl]sulfonyl}-4-piperidinyl)-1H-indole-7-carboxamide or vehicle (0.5% (w/v) aqueous hydroxypropylmethylcellulose containing 0.1% (w/v) Tween 80) were given orally, by gavage, on two consecutive days to groups of 6 male rats. The positive control, cyclophosphamide, was given orally, by gavage, once only to 3 male rats. All rats were killed 24 hours after receiving their final dose and femoral bone marrow smears prepared. Smears were stained with acridine orange prior to analysis with fluorescense microscopy to determine the proportion of polychromatic erythrocytes in the total erythrocyte count (% PCE) and the number of micronucleated polychromatic erythrocytes (MPCE) per 2000 PCE analysed.

Results

The compound of formula (I) was tested for activity against IKK2 in the IKK2 assay and was found to be an inhibitor of IKK2 with $pIC_{50}$ potency of greater than 7.0.

The compound of formula (I) was tested for activity against IKK2 in the IKK2 assay and the IKK2 time dependent assay, and against IKK1 in the IKK1 time-resolved fluorescence resonance energy transfer assay. The compound of formula (I) inhibited IKK2 with greater potency than IKK1.

The compound of formula (I) has $pIC_{50}$ potency of greater than 7.5 in the human peripheral blood mononuclear cell assay.

The compound of formula (I) has $pIC_{50}$ potency of greater than 6.5 in the human whole blood assay.

The compound of formula (I) has $pIC_{50}$ potency of greater than 7.5 in the NFkB reporter assay.

The compound of formula (I) was tested in the in vivo model relating to inhaled LPS induced neutrophilia in the male CD rat. The compound of formula (I) showed a greater than 75% inhibition at a dose of 300 ug/kg i.t.

The compound of formula (I) was tested in vivo in the rat bone marrow micronucleus assay. The compound of formula (I) was not genotoxic in vivo following two oral doses of 1000 or 2000 mg/kg/day, given 24 hours apart. The highest dose tested was the maximum permissible dose in accordance with current guidelines, for example EC Commission Directive 2000/32/EC Annex 4C.

TABLE 2

Rat Bone Marrow Micronucleus Assay Results

| Test Article | Dose[1] (mg/kg/day) | No. of Animals Analysed | Group Mean % PCE | Group Mean MPCE[2] |
|---|---|---|---|---|
| Vehicle control | 0 | 6 Males | 52 | 3.12 |
| Compound of formula (I) | 1000 | 6 Males | 41 | 1.31 |
| Compound of formula (I) | 2000 | 6 Males | 38 | 2.46 |
| Cyclophosphamide[3] | 20 | 3 Males | 46 | 51.87 |

[1]Expressed in terms of the compound of formula (I)
[2]Group mean micronucleated PCE (MPCE) per 2000 PCE analysed
[3]Positive control induced an unequivocal positive response

The invention claimed is:

1. 5-[2-(1-Methylethyl)-2,3-dihydro-1H-isoindol-5-yl]-3-(1-{[2-(methyloxy)ethyl]sulfonyl}-4-piperidinyl)-1H-indole-7-carboxamide of formula (I):

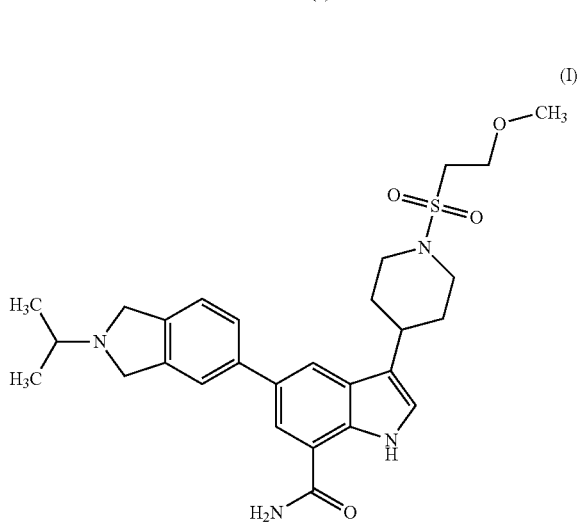

or a salt thereof.

2. 5-[2-(1-Methylethyl)-2,3-dihydro-1H-isoindol-5-yl]-3-(1-{[2-(methyloxy)ethyl]sulfonyl}-4-piperidinyl)-1H-indole-7-carboxamide of formula (I):

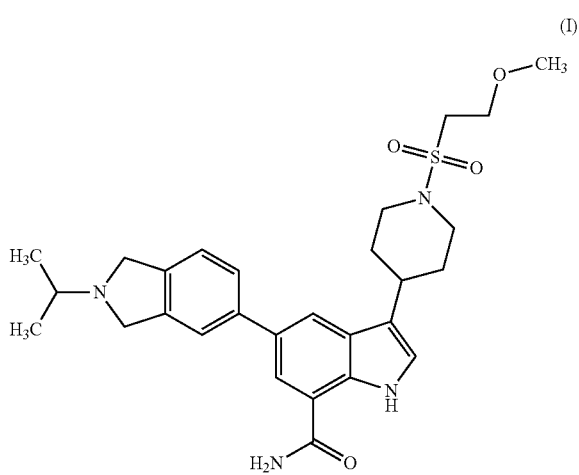 [SMILES: COCCS(=O)(=O)N1CCC(c2c[nH]c3c(C(N)=O)cc(-c4ccc5c(c4)CN(C(C)C)C5)cc23)CC1]

or a pharmaceutically acceptable salt thereof.

3. 5-[2-(1-Methylethyl)-2,3-dihydro-1H-isoindol-5-yl]-3-(1-{[2-(methyloxy)ethyl]sulfonyl}-4-piperidinyl)-1H-indole-7-carboxamide of formula (I):

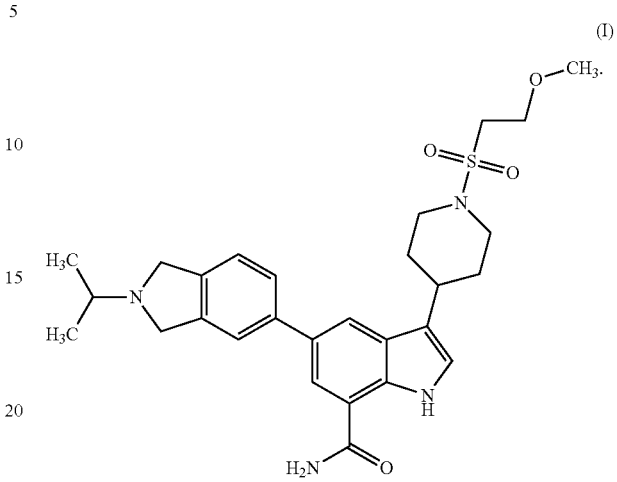

4. A crystalline form of a compound according to claim 2.

5. A crystalline form of the compound according to claim 3, characterised in that it provides:
   (i) An XRPD (X-ray powder diffraction) pattern having peaks (°2θ) at about 6.4, about 7.4, about 12.4, about 15.6 and about 20.5; and/or
   (ii) a DSC (differential scanning calorimetry) thermogram having a melt with combined degredation with an onset temperature of about 115° C.

6. A crystalline form of the compound according to claim 3, characterised in that it provides:
   (i) an XRPD (X-ray powder diffraction) pattern having peaks (°2θ) at 6.4±0.1°2θ, 7.4±0.1°2θ, 12.4±0.1°2θ, 15.6±0.1°2θ and 20.5±0.1°2θ; and/or
   (ii) a DSC (differential scanning calorimetry) thermogram having a melt with combined degredation with an onset temperature of 115° C.

7. A pharmaceutical composition comprising a compound as claimed in claim 2, or a pharmaceutically acceptable salt thereof, and one or more pharmaceutically acceptable excipients.

8. A pharmaceutical composition according to claim 7, which comprises another therapeutically active agent.

9. A combination comprising a) a compound as defined in claim 2, and b) one or more other therapeutic agents.

10. A combination according to claim 9, wherein the one or more other therapeutic agents are selected from the group consisting of: anti-inflammatory agents, anticholinergic agents, β₂-adrenoreceptor agonists, antiinfective agents, and antihistamines.

* * * * *